United States Patent
Chen et al.

(10) Patent No.: US 10,687,896 B2
(45) Date of Patent: Jun. 23, 2020

(54) COMPUTER-AIDED PLANNING OF LIVER SURGERY

(71) Applicants: AGENCY FOR SCIENCE, TECHNOLOGY AND RESEARCH, Singapore (SG); NATIONAL UNIVERSITY HOSPITAL (SINGAPORE) PTE LTD, Singapore (SG)

(72) Inventors: Wenyu Chen, Singapore (SG); Sudhakar K. Venkatesh, Singapore (SG); Qi Tian, Singapore (SG); Jianyin Zhou, Singapore (SG); Weimin Huang, Singapore (SG); Wei Xiong, Singapore (SG); Oo Thiha, Singapore (SG)

(73) Assignees: Agency for Science, Technology and Research, Singapore (SG); National University Hospital (Singapore) Pte Ltd., Singapore (SG)

( * ) Notice: Subject to any disclaimer, the term of this patent is extended or adjusted under 35 U.S.C. 154(b) by 589 days.

(21) Appl. No.: 14/898,059

(22) PCT Filed: Jun. 11, 2014

(86) PCT No.: PCT/SG2014/000272
§ 371 (c)(1),
(2) Date: Dec. 11, 2015

(87) PCT Pub. No.: WO2014/200434
PCT Pub. Date: Dec. 18, 2014

(65) Prior Publication Data
US 2016/0143697 A1    May 26, 2016

(30) Foreign Application Priority Data
Jun. 11, 2013   (SG) ................ 201304503-4

(51) Int. Cl.
*A61F 9/008* (2006.01)
*A61B 34/10* (2016.01)
(Continued)

(52) U.S. Cl.
CPC .............. *A61B 34/10* (2016.02); *A61B 6/032* (2013.01); *A61B 6/5217* (2013.01); *G06F 17/13* (2013.01);
(Continued)

(58) Field of Classification Search
CPC ....... A61B 34/10; A61B 6/032; A61B 6/5217; G06F 17/13; G06F 17/17; G06F 19/3437; G06T 19/00
See application file for complete search history.

(56) References Cited

U.S. PATENT DOCUMENTS

| 2006/0282162 | A1* | 12/2006 | Nguyen | ................ | A61F 2/2445 623/2.11 |
| 2007/0249967 | A1* | 10/2007 | Buly | .................... | A61B 5/1121 600/595 |
| 2008/0039742 | A1 | 2/2008 | Hashimshony et al. | | |
| 2008/0118136 | A1 | 5/2008 | Cai et al. | | |

(Continued)

FOREIGN PATENT DOCUMENTS

WO    2014200434 A1    12/2014

OTHER PUBLICATIONS

Duan et al., "Shape Reconstruction from 3D and 2D Data Using PDE-Based Deformable Surfaces," Lecture Notes in Computer Science, vol. 3023, 2004 pp. 238-251.
(Continued)

*Primary Examiner* — Brian W Wathen
*Assistant Examiner* — Abdou K Seye
(74) *Attorney, Agent, or Firm* — Conley Rose, P.C.

(57) ABSTRACT

A method for surgical resection planning of a mass includes the steps of, modelling the mass based on a plurality of physical dimensions, determining a plurality of safety mar-
(Continued)

100 gins around a plurality of features within the mass, simulating a resection surface on the mass that includes a plurality of triangles, optimizing local area and position of a first of the plurality of triangles on the resection surface based on a triangle-based algorithm, updating the simulation of the resection surface, and repeating the steps of optimizing and updating for each of the plurality of triangles on the resection surface.

20 Claims, 21 Drawing Sheets

(51) Int. Cl.
| | | |
|---|---|---|
| *A61B 6/03* | (2006.01) | |
| *G06T 19/00* | (2011.01) | |
| *A61B 6/00* | (2006.01) | |
| *G16H 50/50* | (2018.01) | |
| *G06F 17/13* | (2006.01) | |
| *G06F 17/17* | (2006.01) | |

(52) U.S. Cl.
CPC .............. *G06F 17/17* (2013.01); *G06T 19/00* (2013.01); *G16H 50/50* (2018.01); *A61B 2034/101* (2016.02); *A61B 2034/105* (2016.02); *A61B 2034/107* (2016.02); *G06T 2210/41* (2013.01); *G06T 2219/008* (2013.01)

(56) References Cited

U.S. PATENT DOCUMENTS

| | | | | |
|---|---|---|---|---|
| 2008/0123927 | A1* | 5/2008 | Miga | A61B 90/36 382/131 |
| 2010/0316268 | A1* | 12/2010 | Liang | G06T 19/00 382/128 |
| 2012/0053443 | A1* | 3/2012 | Sakuragi | A61B 19/50 600/407 |
| 2012/0209106 | A1 | 8/2012 | Liang et al. | |
| 2013/0063434 | A1* | 3/2013 | Miga | A61B 90/36 345/420 |
| 2013/0163836 | A1* | 6/2013 | Pau | G06T 7/00 382/128 |

OTHER PUBLICATIONS

Saito et al., "A Novel 3D Hepatectomy Simulation Based on Liver Circulation: Application to Liver Resection and Transplantation," Hepatology, vol. 41, No. 6, 2005, published Jun. 2005, pp. 1297-1304, 2 p., Abstract only.

Mei et al., "T-Base: A Triangle-Based iterative Algorithm for Smoothing Quadrilateral Meshes," Proceedings of the 2012 International Conference on Information and Technology and Software Engineering, Lecture Notes in Electrical Engineering, vol. 212, 2013, pp. 305-315, Nov. 6, 2012, 2 p. Abstract only.

Astar et al, International Preliminary Report on Patentability dated Oct. 1, 2015, PCT App. No. PCT/SG2014/000272, 27 p.

Astar et al., International Search Report dated Aug. 14, 2014, PCT App. No. PCT/SG2014/000272, 5 p.

* cited by examiner

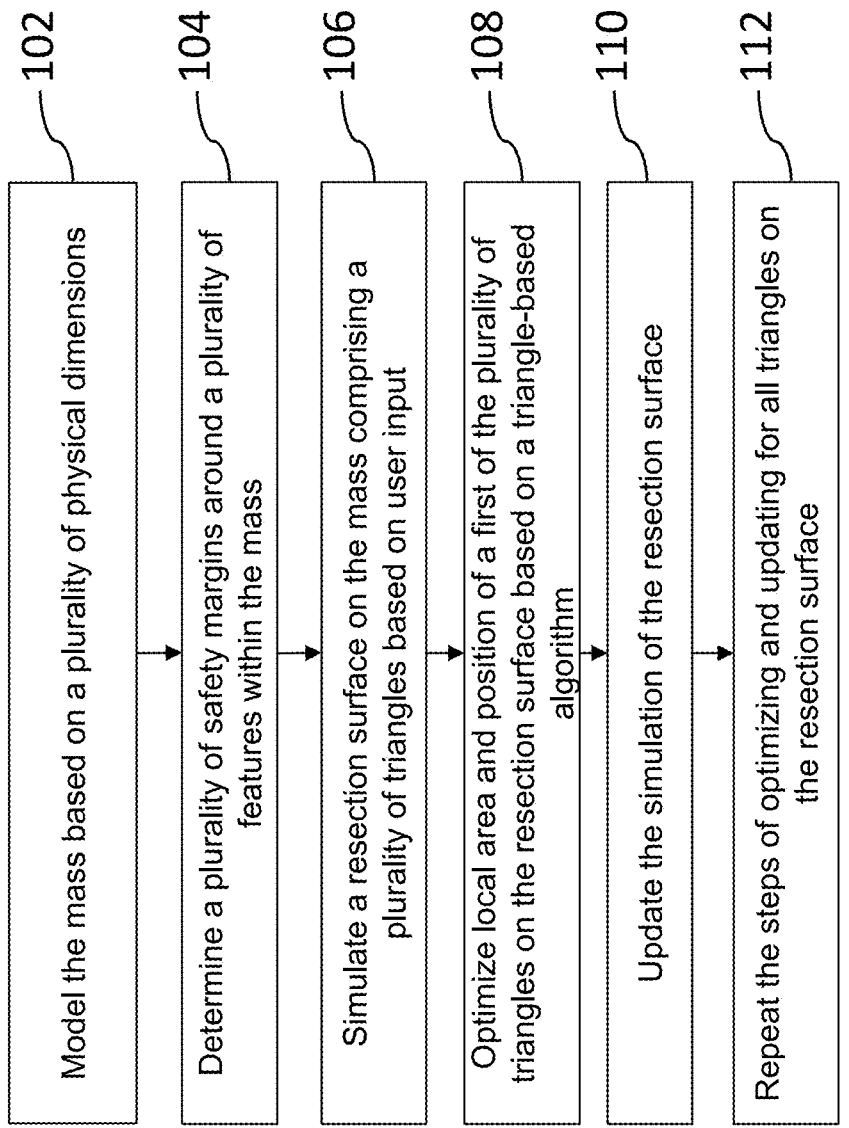

200

250

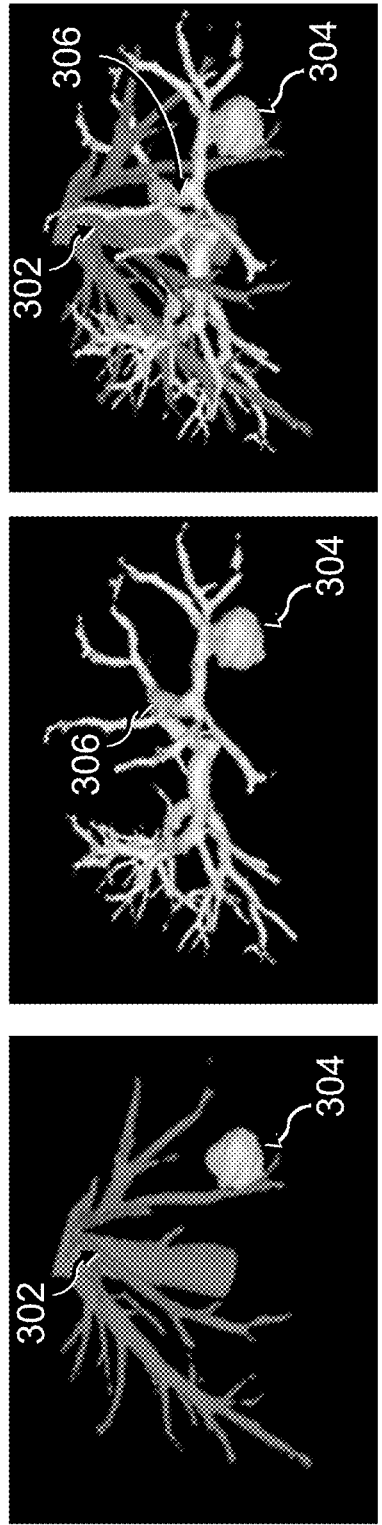

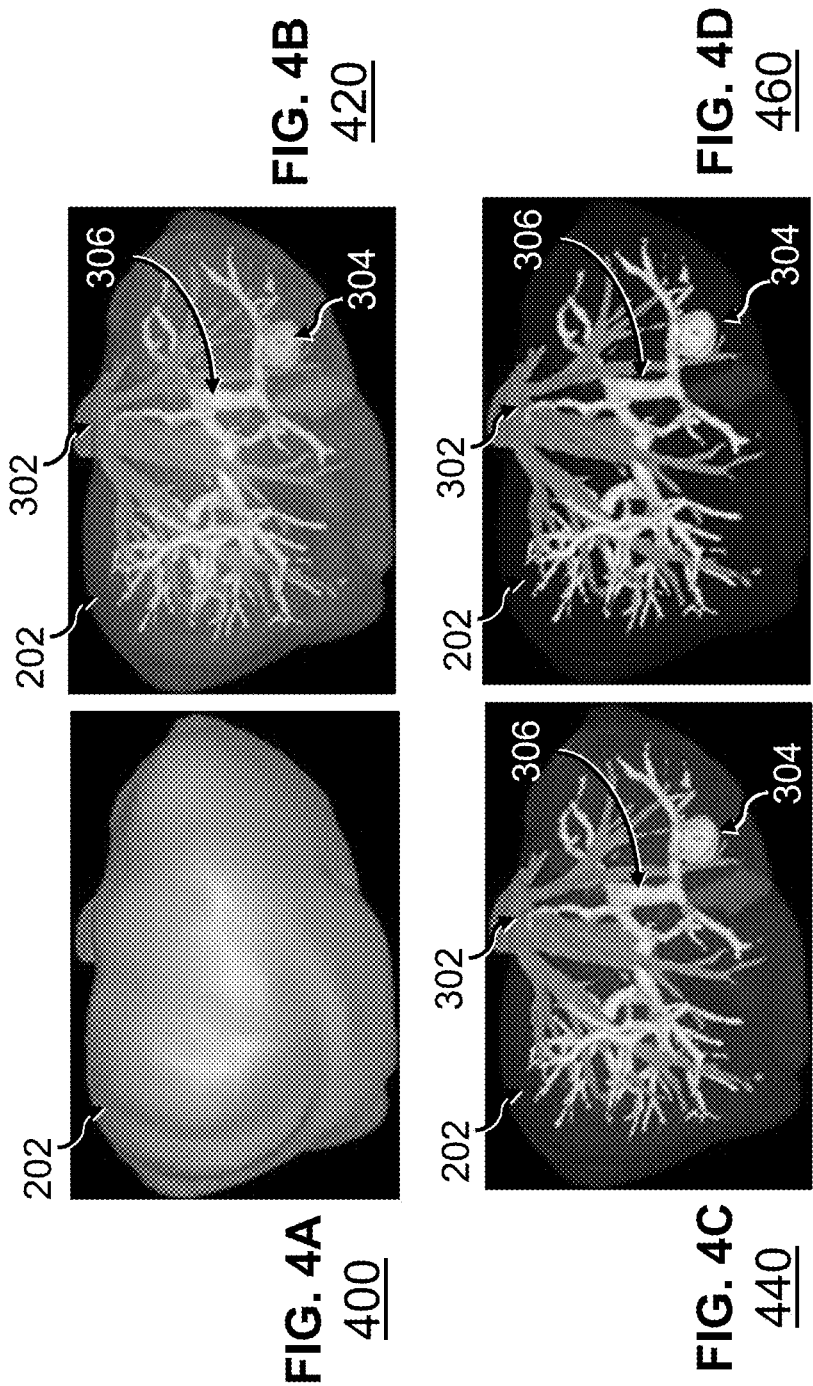

500

520

540

560

600

700

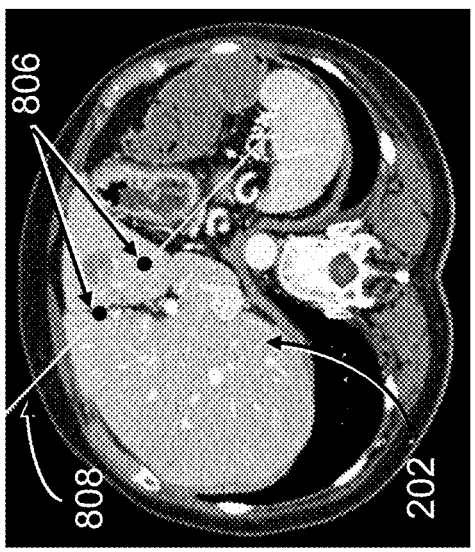
FIG. 8A 800
FIG. 8B 820
FIG. 8C 830
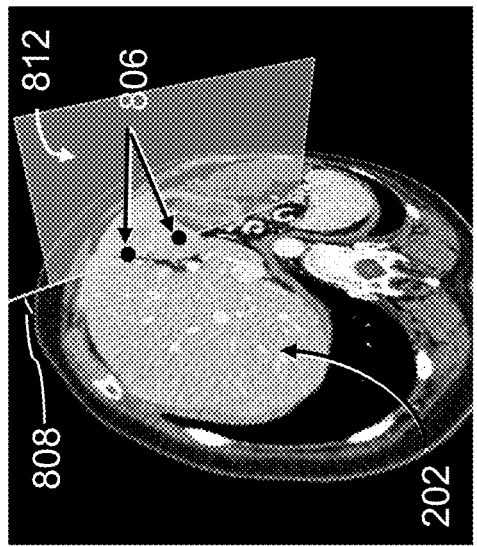
FIG. 8D 840
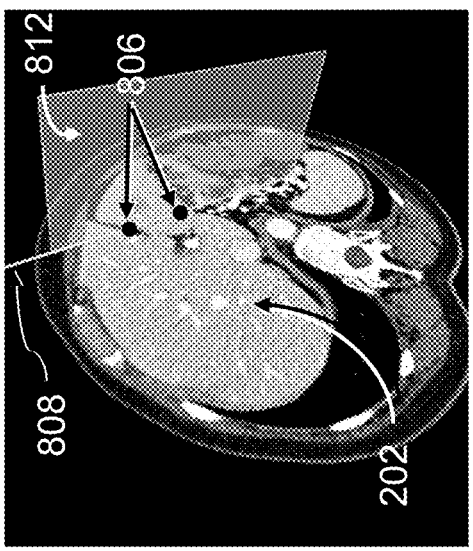
FIG. 8E 860
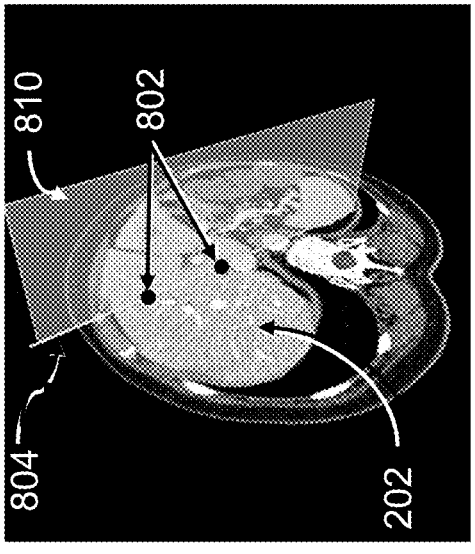
FIG. 8F 870

940

920

900

1000

1020

1040

1060

1100

1150

1200

1400

1500

1700

1800

COMPUTER-AIDED PLANNING OF LIVER SURGERY

CROSS-REFERENCE TO RELATED APPLICATION

The present application is the U.S. National Stage under 35 U.S.C. § 371 of International Patent Application No. PCT/SG2014/000272, filed Jun. 11, 2014, which claims priority to Singapore Application No. SG 201304503-4, filed Jun. 11, 2013, the disclosures of which are hereby incorporated herein by reference.

FIELD OF THE INVENTION

The present invention relates to computer-aided surgery planning. In particular, it relates to computer-aided planning of liver resection surgery.

BACKGROUND

The liver is a vital organ of the digestive system which performs a wide range of functions, including protein synthesis, hormone production and glycogen storage. It consists of four lobes of unequal size and shape, and is connected to two major blood vessels, the hepatic vein and the portal vein. Liver resections, also referred to as hepatectomies, are performed for the treatment of malignant neoplasms, including hepatocellular carcinoma (HCC) and/or metastasis commonly arising from colorectal cancer. Hepatectomies may also be performed to treat intrahepatic gallstones or parasitic cysts of the liver.

Traditional liver surgery planning is based on visual observation of a series of two-dimensional (2D) computed tomography (CT) images. Before a hepatectomy, the radiologist or surgeon needs to characterize the anatomic structure of the patient's liver and its components. The hepatic vein, the portal vein, functional lobes and the cancer tumors have to be identified and located on the 2D CT images. This process is known as segmentation. Following the segmentation step, a resection curve is drawn on the 2D CT images by the radiologist or surgeon. This process is manually intensive and time consuming. Furthermore, the success of traditional liver surgery planning is highly dependent on the skill of the radiologist and/or surgeon. Moreover, while most radiologists prefer surgery planning by drawing resection curves on different 2D CT images, many surgeons are naturally three dimensionally (3D) oriented, rendering it difficult for surgeons to perform liver surgery planning based on traditional 2D radiological methods.

Automated liver surgery planning systems have been developed to identify anatomical, pathological and functional parts of the liver from 2D CT scans, to visualize a 3D model of the liver, and to generate a resection proposal for the surgeon. Computer-aided liver surgery planning systems may also propose a safety margin around specific hepatic features such as the portal vein and the hepatic vein, or propose a resection plan based on a required resection volume. However, the current computer-aided liver surgery planning systems are complicated, preventing untrained surgeons from utilizing the systems effectively. In addition, the accuracy and success of the simulation is highly dependent on the initial data that is provided by the user and is still dependent upon the skill of the radiologist and/or surgeon.

Thus, what is needed is an improved computer-aided liver surgery planning system that is easy to use and produces an optimized, customizable and robust liver resection proposal for the user. Furthermore, other desirable features and characteristics will become apparent from the subsequent detailed description and the appended claims, taken in conjunction with the accompanying drawings and this background of the disclosure.

SUMMARY

In a first aspect of the present invention, a method for surgical resection planning of a mass is disclosed, the method comprising the steps of modelling the mass based on a plurality of physical dimensions, determining a plurality of safety margins around a plurality of features within the mass, simulating a resection surface on the mass comprising a plurality of triangles, optimizing local area and position of a first of the plurality of triangles on the resection surface based on a triangle-based algorithm, updating the simulation of the resection surface and repeating the steps of optimizing and updating for each of the plurality of triangles on the resection surface.

In a second aspect of the present invention, a computer readable storage medium is disclosed, the computer readable storage medium having a computer program recorded therein, the program being executable by a computer apparatus to make the computer perform the procedure of surgical resection planning of a mass, the procedure comprising the steps of, modelling the mass based on a plurality of physical dimensions, determining a plurality of safety margins around a plurality of features within the mass, simulating a resection surface on the mass comprising a plurality of triangles, optimizing local area and position of a first of the plurality of triangles on the resection surface based on a triangle-based algorithm, updating the simulation of the resection surface and repeating the steps of optimizing and updating for each of the plurality of triangles on the resection surface.

BRIEF DESCRIPTION OF THE DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with the present embodiment.

FIG. 1 depicts a flowchart of a method embodying computer-aided surgery planning in accordance with a present embodiment.

FIG. 2, comprising FIG. 2A and FIG. 2B, illustrates segmentation of the liver using computed tomography (CT) images, in accordance with the present embodiment, wherein FIG. 2A illustrates a CT image of the liver before segmentation, and FIG. 2B illustrates a CT image of the liver after segmentation.

FIG. 3, comprising FIG. 3A to FIG. 3C, illustrates three dimensional (3D) visualization of several features within a liver based on segmentation of CT images of the liver, in accordance with the present embodiment, wherein FIG. 3A illustrates a hepatic vein and a tumor within the liver, FIG. 3B illustrates a portal vein and the tumor within the liver, and FIG. 3C illustrates the hepatic vein, portal vein and tumor within the liver.

FIG. 4, comprising FIG. 4A to FIG. 4D, illustrates 3D visualization of a liver and features within the liver using different transparencies, in accordance with the present embodiment, wherein FIG. 4A to FIG. 4D illustrates 3D visualization of the liver using no transparency, 60% transparency, 80% transparency, and 90% transparency respectively.

FIG. 5, comprising FIG. 5A to FIG. 5D, illustrates a combination of two dimensional (2D) CT image and 3D visualization of a liver and features within the liver, in accordance with the present embodiment, wherein FIG. 5A and FIG. 5C are 2D CT images without 3D visualization overlay, and FIG. 5B and FIG. 5D are the respective 2D CT images with 3D visualization overlay.

FIG. 8, comprising FIG. 8A to FIG. 8F, illustrates interactive surgery planning using a planar resection surface, in accordance with the present embodiment, wherein FIGS. 8A to 8C illustrate 2D CT visualizations of planar resection simulation results on a 2D CT image slice as defined by the user, and FIGS. 8D to 8F illustrate 3D visualizations of the planar resection plan on the 2D CT image slice.

FIG. 9, comprising FIG. 9A to FIG. 9C, illustrates planar resection simulation results through 2D CT image slices of a liver, in accordance with the present embodiment, wherein FIG. 9A illustrates a first 2D CT image slice of the liver, and FIG. 9B and FIG. 9C illustrate subsequent 2D CT image slices along an axis of the liver.

FIG. 10, comprising FIG. 10A to FIG. 10D, illustrates interactive surgery planning using a planar resection surface, in accordance with the present embodiment, wherein FIG. 10A and FIG. 10B illustrate two points in a visualization space defined by a user to initialize a planar resection plan, and FIG. 10C and FIG. 10D illustrate a combined 2D CT image and 3D visualization of the planar resection plan the liver in accordance with the present embodiment.

FIG. 11, comprising FIG. 11A and FIG. 11B, illustrates interactive surgery planning using a planar resection surface, in accordance with the present embodiment, wherein FIG. 11A and FIG. 11B illustrate combined 2D CT image slice and 3D visualization of the planar resection plan.

FIG. 13, comprising FIG. 13A to FIG. 13I, illustrates interactive surgery planning using a swept resection surface, in accordance with the present embodiment, wherein FIG. 13A to FIG. 13I illustrate a 3D visualization of a sequence of steps performed in interactive surgery planning using a swept resection surface.

FIG. 14, comprising FIG. 14A to FIG. 14F, illustrates interactive surgery planning using a swept resection surface for hemihepatectomy, in accordance with the present embodiment, wherein FIG. 14A to FIG. 14F illustrate several 3D visualization views of the swept resection plan.

FIG. 16A to FIG. 16C, illustrates interactive surgery planning using a freeform resection surface, in accordance with the present embodiment, wherein FIG. 16A to FIG. 16C illustrate a 3D visualization of a sequence of steps performed in interactive surgery planning using a freeform resection surface.

FIG. 19, comprising FIG. 19A to FIG. 19C, illustrates modelling a resection surface as a plurality of triangles, in accordance with the present embodiment, wherein FIG. 19A illustrates the resection surface with the tumor, FIG. 19B illustrates the resection surface without the tumor, and FIG. 19C illustrates a close up of the selected triangle.

FIG. 20, comprising FIG. 20A to FIG. 20D, illustrates a 3D visualization of the safety margin around a tumor, in accordance with the present embodiment, wherein FIG. 20A and FIG. 20B illustrate an increase in the safety margin around a tumor from 5 millimeters (mm) to 10 mm, respectively, and FIG. 20C and FIG. 20D illustrate a corresponding position of a resection surface with 5 mm and 10 mm safety margin around the tumor, respectively.

FIG. 21, comprising FIG. 21A to FIG. 21E, illustrates another 3D visualization of the safety margin around a tumor, in accordance with the present embodiment, wherein FIG. 21A and FIG. 21B illustrate the distance between the tumor and the hepatic vein, and FIG. 21C to FIG. 21E illustrate a corresponding position of a resection surface when the safety margin around the tumor is increased from 1 mm to 1.5 mm, and to 2 mm, respectively.

Figure 2A:
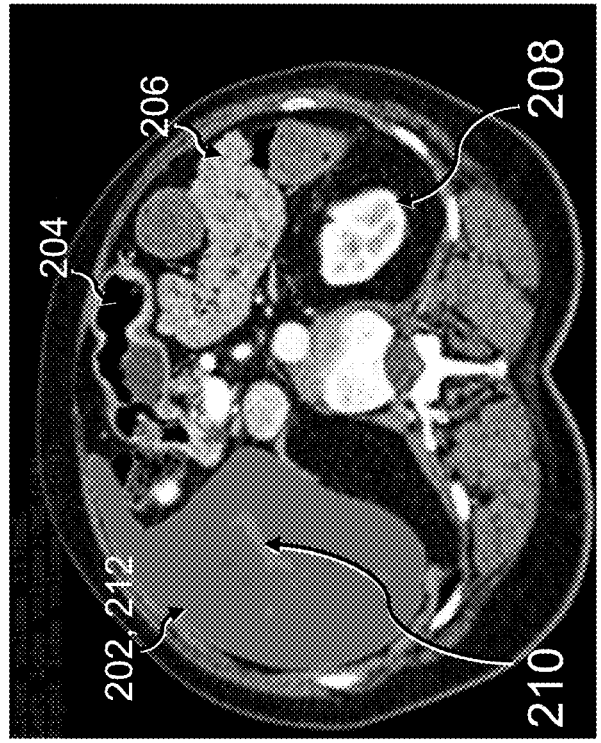

Skilled artisans will appreciate that elements in the figures are illustrated for simplicity and clarity and have not necessarily been depicted to scale. For example, the dimensions of some of the elements in the simulation visualization or steps in the flowcharts may be exaggerated in respect to other elements to help improve understanding of the present embodiment.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description. It is the intent of the present embodiment to present an improved computer-aided liver surgery planning system that is easy to use and guarantees safety margins of the proposed resection.

FIG. 1 depicts a flowchart of a method embodying computer-aided surgery planning in accordance with the present embodiment. At step 102, the mass is modelled based on a plurality of physical dimensions. The physical dimensions of the liver and the internal features may be modelled using data from two dimensional (2D) computed tomography (CT) images. At step 104, a plurality of safety margins around a plurality of features within the mass is determined. The features within the mass include the hepatic vein, the portal vein or tumor, for example. The safety margin is the smallest distance that any point on the resection surface may come into proximity with the feature. This is to ensure that the simulated resection surface guarantees this safety margin to accommodate for human error during the operation itself. At step 106, a resection surface comprising a plurality of triangles is simulated on the mass. The user may make adjustments to the boundary of the resection surface or change the safety margins. At step 108, local area and position of a first of the plurality of triangles on the resection surface is optimized based on a triangle-based algorithm. At step 110, the simulation of the resection surface is updated. At step 112, the steps of optimizing 108 and updating 110 are repeated for all triangles on the resection surface. The use of the triangle based algorithm to optimize the resection surface provides a fast and efficient way to minimize the local area and guarantee the safety margins around the features within the liver.

The present embodiment provides several advantages to the user. Interactive editing is important for surgeons or radiologists to perform the planning as it provides an intuitive and simple means for users to simulate a liver resection. In conventional simulations, users are required to label a set of markers on or inside the liver. This is inconvenient for the user as there are many parameters and variables involved in the simulation and introduces possible sources of error. Moreover, conventional simulations do not guarantee that the safety margins around features within the liver are not compromised by the simulated resection surface. The simulation in the present embodiment allows for easy user interaction. Users only need to adjust the boundary of the resection surface or the safety margins around the features in order to update the simulated resection surface. Accordingly, the present embodiment advantageously provides an easier and a more robust method of liver resection planning.

Moreover, in conventional systems, the safety margin around features within the liver is not guaranteed without additional inputs or user modification to the simulated resection proposal. Users need to manually check that the simulated resection surface does not compromise the safety margins, and make manual changes to the resection surface thereafter. In the present embodiment, the simulation in the present embodiment generates resection surfaces that guarantee the safety margin to features within the liver automatically. Users do not need to edit the resection surface to ensure that the resection surface is outside of the safety margin as this is performed automatically by the simulation. Accordingly, the present embodiment provides an easier and more user friendly interaction than conventional simulations.

The present embodiment provides automatic resection surface area minimization based on a triangle-based algorithm. A minimized resection surface simulation is advantageous as minimizes the invasiveness of the resection and reduces blood loss during the surgery. This allows faster recovery time for the patient and minimizes the chances of complications post-surgery.

Figure 2B:
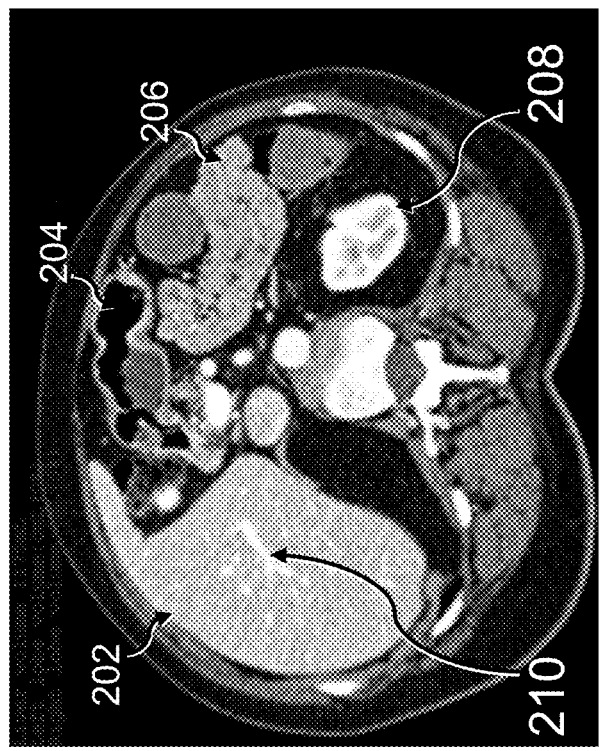

The physical dimensions of the liver and the internal features may be modelled using data from 2D CT images. FIG. 2, comprising FIG. 2A and FIG. 2B, illustrates segmentation of the liver using CT images, in accordance with the present embodiment, wherein FIG. 2A illustrates a CT image of the liver before segmentation 200, and FIG. 2B illustrates a CT image of the liver after segmentation 250. Segmentation is the digital process by which features such as the liver, the body of the stomach 204, the spleen 206 and the left or right kidney 208, in the raw CT image 200 are identified. In addition, features within the liver 202 such as the portal vein 210 and the hepatic vein (not shown) may also be identified in this step. After segmentation, these features may be highlighted in a processed CT image 250 with a different color 212 in preparation for further processing.

Segmentation of CT images may be performed using probabilistic vessel axis and level sets-based methods, CT angiography of images, particle filter based techniques, minimum cost path, region growing algorithms or topological methods. Alternatively, vessel context-based voting algorithms may be used to segment and identify liver vasculatures using region-based features.

After segmentation, the features within the liver 202 may be visualized as 2D or three dimensional (3D) forms. FIG. 3, comprising FIG. 3A to FIG. 3C, illustrates 3D visualization 300, 320, 340, of several features 302, 304, 306, within a liver (not shown) based on segmentation of CT images of the liver, in accordance with the present embodiment, wherein FIG. 3A illustrates a hepatic vein 302 and a tumor 304 within the liver (not shown), FIG. 3B illustrates a portal vein 306 and the tumor 304 within the liver (not shown), and FIG. 3C illustrates the hepatic vein 302, portal vein 306 and tumor 304 within the liver (not shown). Users may choose any combination of the liver features to be visualized. This may help users not only to understand the relationship between the tumor 304 and the vessels 302, 306, but also to see how different features 302, 304, 306 of the liver (not shown) would be affected by a resection to remove the tumor 304.

In another embodiment, the liver 202 and internal features 302, 304, 306, may be modelled and visualized in 3D as a single model. FIG. 4, comprising FIG. 4A to FIG. 4D, illustrates 3D visualization 400, 420, 440, 460, of a liver 202 and features within the liver 302, 304, 306, using different transparencies, in accordance with the present embodiment, wherein FIG. 4A to FIG. 4D illustrates 3D visualization of the liver using no transparency 400, 3D visualization of the liver using 60% transparency 420, 3D visualization of the liver using 80% transparency 440, and 3D visualization of the liver using 90% transparency 460 respectively. Presenting the liver 202 and features within the liver 302, 304, 306, using different transparencies are advantageous for the user to relate the structure and morphology of the liver 202 with the position of the features 302, 304, 306, within the liver 202.

Figure 5A:
Figure 5B:
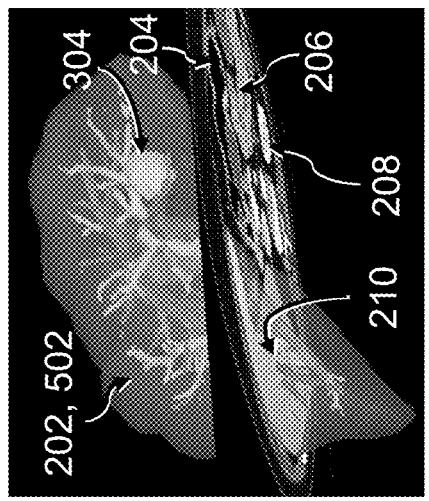
Figure 5C:
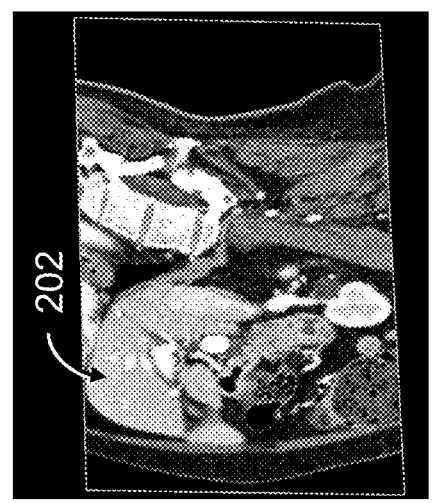
Figure 5D:
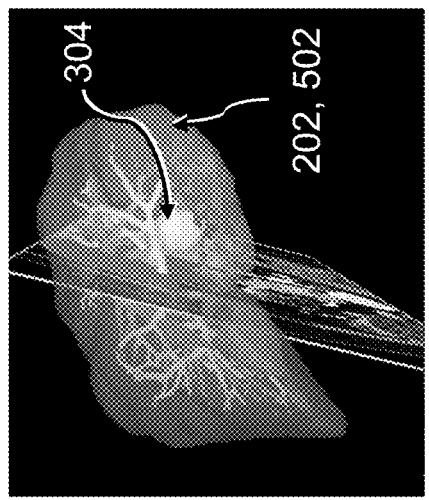

In another embodiment, the liver 202 and internal structures 302, 304, 306, may be modelled and visualized as a combined 2D CT model and a 3D model 502 of the liver 202 using techniques such as blending, 3D texturing and overlaying for example. FIG. 5, comprising FIG. 5A to FIG. 5D, illustrates a combination of 2D CT image and 3D visualization of a liver and features within the liver, in accordance with the present embodiment, wherein FIG. 5A and FIG. 5C are 2D CT images without 3D visualization overlay 500, 540, and FIG. 5B and FIG. 5D are the respective 2D CT images with 3D visualization overlay 520, 560. Comprehensive visualization techniques allow the user to identity the structure and morphology of the liver 202 relative to the position of other organs 206, 208 or features 210 within the liver 202. Presenting an overlay of 2D CT and 3D visualization data provides an intuitive and comprehensive model to the user for ease of reference.

Figure 6:
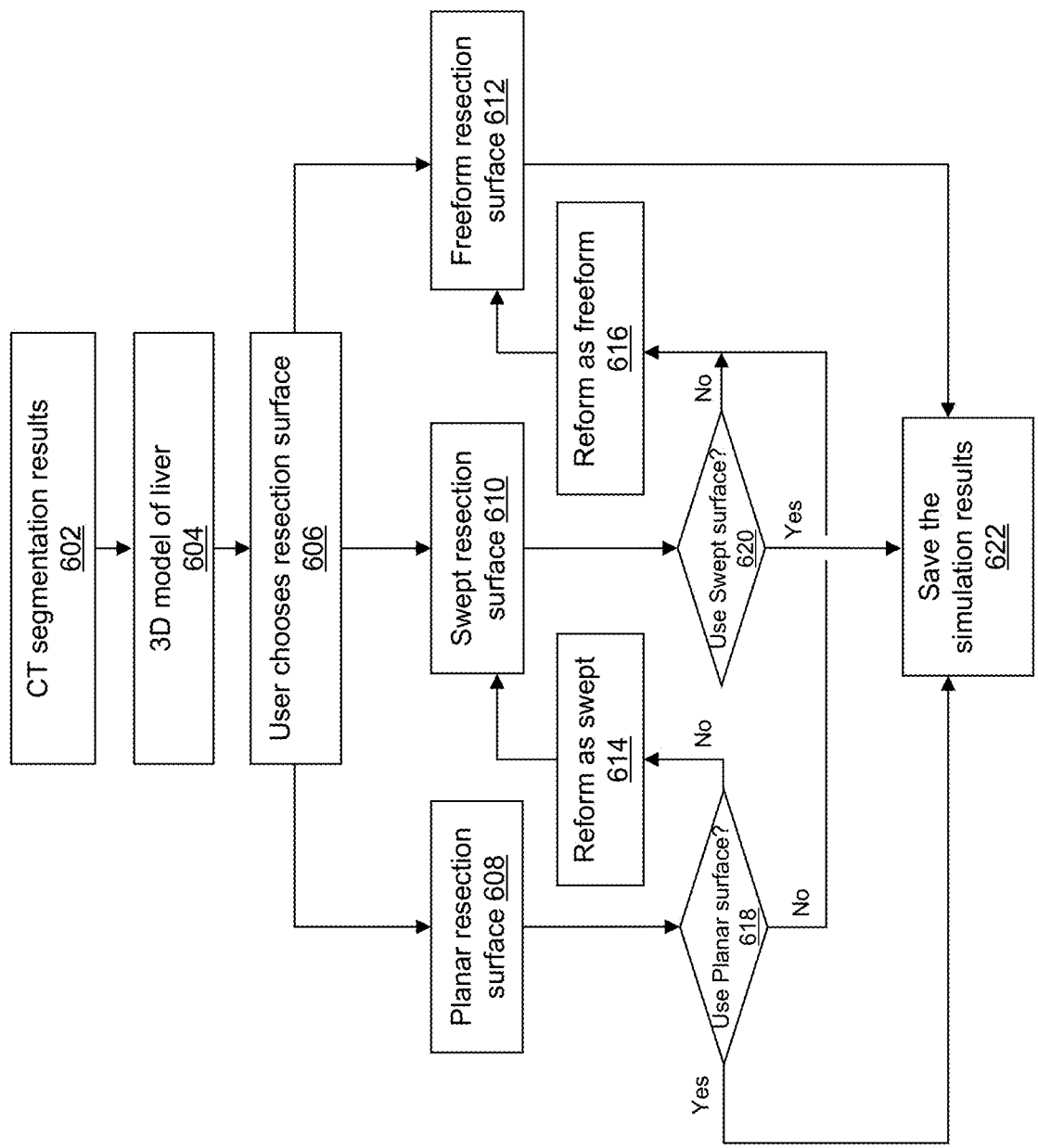
FIG. 6 depicts a flowchart embodying interactive surgery planning utilizing several resection forms in accordance with the present embodiment.

FIG. 6 depicts a flowchart embodying interactive surgery planning utilizing several resection forms in accordance with the present embodiment. At step 602, the CT segmentation results of the 2D CT images are used to create a 3D model of the liver. The user may choose 606 between a plurality of resection surfaces including planar resection surface, swept resection surface and freeform resection surface for the resection simulation. A simulation is performed based on the user's choice of resection surface, generating a planar resection surface 608, swept resection surface 610 or freeform resection surface 612. If the planar resection surface is chosen 618 the simulation is finalized and the resection plan is saved 622.

Alternatively, the user may decide 618 not to use the simulated planar resection surface and reform the planar resection surface as a swept resection surface 614. The simulation may use the data from the planar resection surface 608 as a starting point to simulate the swept resection surface 610. The user again has a choice to use the swept resection surface 620 or to reform the surface as a freeform resection surface 616, 612. The simulation may use the swept surface as a starting point for the freeform resection surface 612. Finally, if the user decides to use the swept surface 610 or the freeform surface 612, the simulation is finalized and the resection plan is saved 622.

Figure 7:
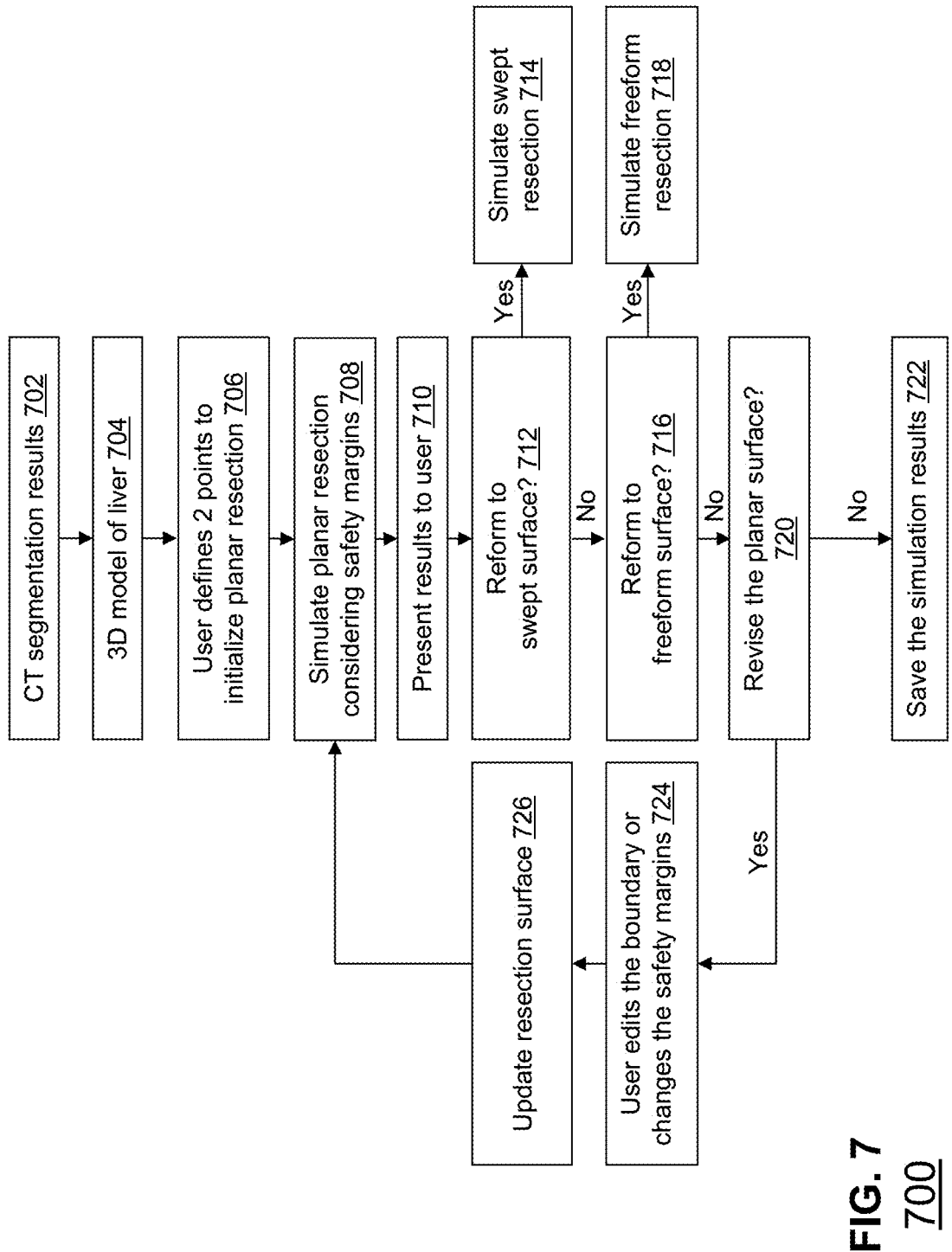
FIG. 7 depicts a flowchart embodying interactive surgery planning using a planar resection surface in accordance with the present embodiment.

FIG. 7 depicts a flowchart embodying interactive surgery planning using a planar resection surface in accordance with the present embodiment. CT segmentation results 702 may be used to derive a 3D model of the liver 704. To initialize the planar resection simulation, the user defines two points in the coordinate space of the 3D model 706. These two points serve as the initial conditions for the simulation to simulate the planar resection. The simulation may consider safety margins around important features within the liver 708, or other conditions that the user has indicated. After the simulation is complete, the planar resection simulation is presented to the user 710. The user may decide if the planar resection surface needs to be reformed into a swept surface 712, or into a freeform surface 716. The simulation will perform the swept resection simulation 714 or the freeform resection simulation 718 based on the simulated planar resection surface, 710, that has been simulated. Alternatively, changes may be made to revise the planar surface 720. The user may edit the boundary of the simulated planar resection surface or change the safety margins around the important features 724. The simulation will subsequently update the resection surface 726 and simulate the planar resection 708 considering the new boundary conditions and safety margins that the user has provided 724. If the user is satisfied with the updated simulation 710, the simulation results are saved for future reference 722.

Users only need to edit the boundary and adjust the safety margin 724 to update the resection surface 726. The simulation will automatically guarantee the safety margin for each tumor. Thus, the user advantageously does not need to input any markers inside the liver or check the safety margins for each tumor as in conventional simulations.

FIG. 8, comprising FIG. 8A to FIG. 8F, illustrates interactive surgery planning using a planar resection surface 804, 808, 810, 812, in accordance with the present embodiment, wherein FIGS. 8A to 8C illustrate 2D CT visualizations of planar resection simulation results on a 2D CT image slice 800, 820 as defined by the user, and FIG. 8D to 8F illustrate 3D visualizations of the planar resection plan on the 2D CT image slice 840, 860. In FIG. 8A, a planar resection simulation 804 is initialized when the user selects two points 802 on the 2D CT image slice 800. The planar resection surface 804 is simulated and projected onto a 2D CT image 800 of the liver 202. The user may refine the planar resection surface by changing the positions of the two points 802 to a new position 806 and the planar resection surface 804 will be updated accordingly 808. In FIG. 8D and FIG. 8E, the 2D CT images 840, 860 may be rotated three dimensionally for the user to view the planar resection surface 810, 812 in 3D. 3D Rotation of the 2D CT image 840, 860 advantageously provides spatial orientation in both 2D and 3D perspectives simultaneously for the user and easier visualization of the planar resection surface 810, 812 in 3D.

In the present embodiment, the user may cycle through a series of 2D CT image slices, after selecting two points 802 to initialize the planar resection simulation. FIGS. 8B and 8E illustrates the first 2D CT image 820 in the series, and corresponding 3D visualization of the 2D CT image 860, on which the initial two points 806 were selected to initialize the resection simulation 808. FIGS. 8C and 8F illustrates the next 2D CT image slice in the series 830, and corresponding 3D visualization of the 2D CT image 870, that shows the user the corresponding position of the two points 806 on this new slice 830, 870. The corresponding position of the two points 802 may be updated on the next image slice 830, 870 for the user to advantageously refine the resection surface 808 on subsequent image slices 830, 870, in the series without being required to refer to the original 2D CT image slice 820, 860.

Figure 9C:
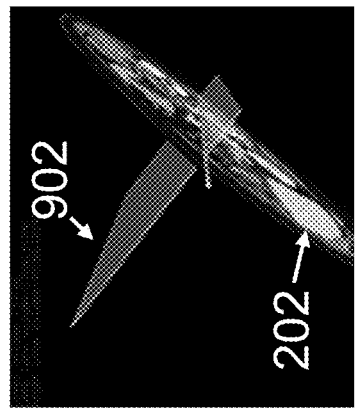
Figure 9B:
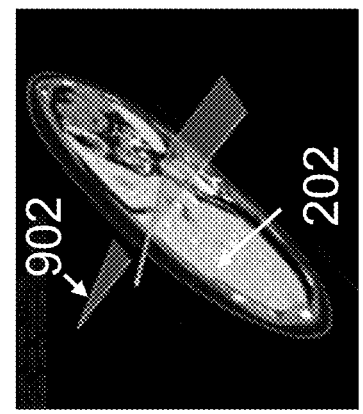
Figure 9A:
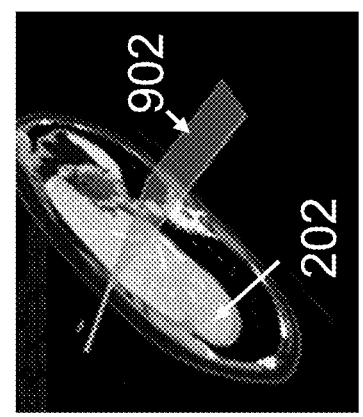

FIG. 9, comprising FIG. 9A to FIG. 9C, illustrates planar resection simulation results through 2D CT image slices of a liver, in accordance with the present embodiment, wherein FIG. 9A illustrates a first 2D CT image slice of the liver, and FIG. 9B and FIG. 9C are subsequent 2D CT image slices along an axis of the liver. The user is able to view the plane resection surface on subsequent 2D CT slices along an axis of the liver 202. Users may initiate planar resection simulation by moving the 2D CT slices relative to the planar resection surface. The planar resection surface on subsequent slices along the axis of the liver slice will be updated automatically. Users may edit the resection surface by editing the intersection line (i.e. trimming line) between the 2D CT and the planar resection surface when necessary. Accordingly, the user only needs to check several 2D CT slices along the axis of the liver to make the final decision. During trimming line editing, the simulation may automatically guarantee that the final planar resection surface maintains the safety margin to the tumor during tumor resection, and the safety margin to the middle hepatic vein (MHV) during hemihepatectomy.

Figure 10A:
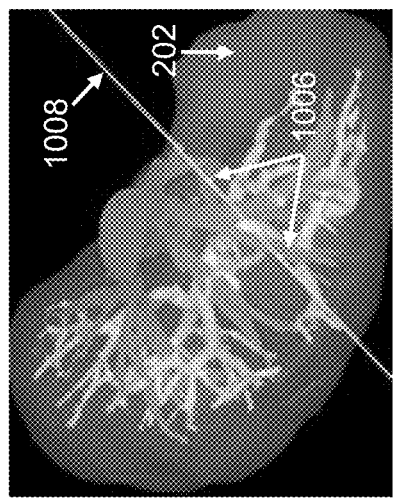
Figure 10B:
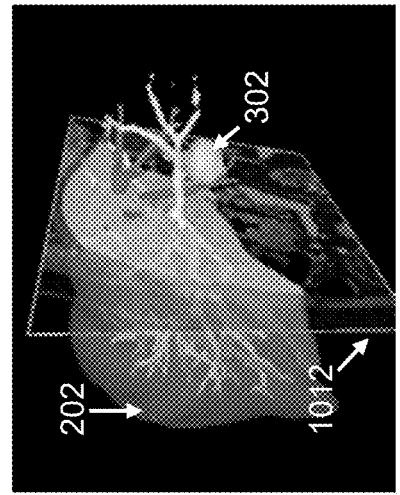
Figure 10C:
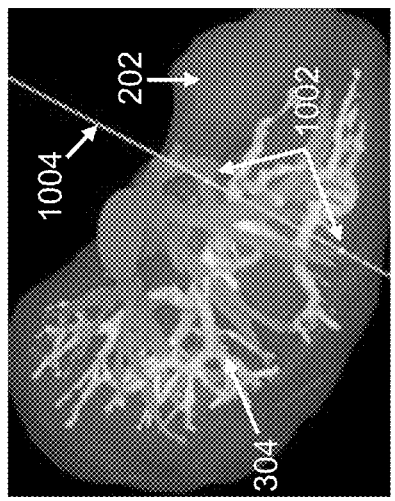
Figure 10D:
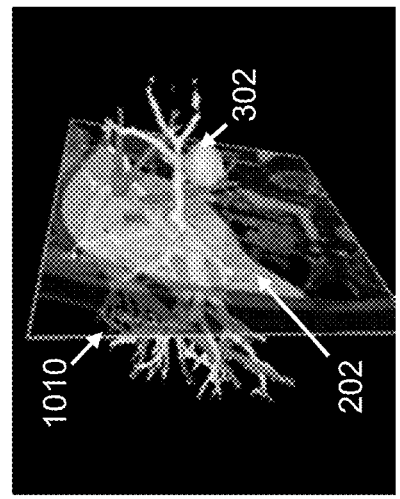

FIG. 10, comprising FIG. 10A to FIG. 10D, illustrates interactive surgery planning using a planar resection surface, in accordance with the present embodiment, wherein FIG. 10A and FIG. 10B illustrate two points 1002, 1006 in a visualization space 1000, 1020, 1040, 1060 defined by a user to initialize a planar resection surface 1004, 1008, and FIG. 10C and FIG. 10D illustrate a combined 2D CT image and 3D visualization of the planar resection surface 1010, 1012 in the liver 202 in accordance with the present embodiment. The user may initiate planar resection simulation 1004, 1008, 1010, 1012 while viewing a 3D visualization of the liver 202 in different perspectives. In the present embodiment, two points may be selected 1002 in the visualization space 1000 to initiate the planar resection simulation 1004. The simulated planar resection surface 1004 will then be projected onto the 3D model. The user may update the planar resection surface 1004 by moving the two points 1002 to a new position 1006. The planar resection surface 1004 will be updated 1008 based on the new conditions. Initialization of the planar resection simulation may be performed in a plurality of perspectives 1004, 1008, 1010, 1012. This provides an easier and a more intuitive means of initializing planar resection simulation. In addition, properties such as the transparency of the 3D model may be adjusted to allow features 302 of the liver 202 that are intersecting with the planar resection surface 1010, 1012 to be seen clearly. FIG. 10C and FIG. 10D illustrates a combined 2D CT image and 3D visualization 1040, 1060 of the planar resection plan.

Figure 11A:
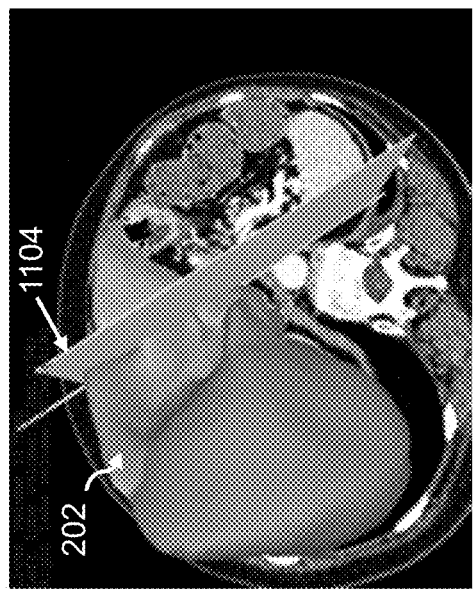
Figure 11B:
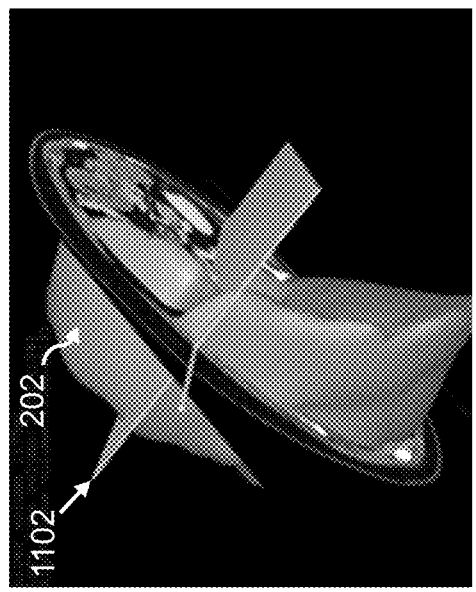

FIG. 11, comprising FIG. 11A and FIG. 11B, illustrates interactive surgery planning using a planar resection surface, in accordance with the present embodiment, wherein FIG. 11A and FIG. 11B illustrate combined 2D CT image slice and 3D visualization of the planar resection plan. The user is able to initiate planar resection simulation 1102, 1104 when viewing the liver 202 as a 3D model with a 2D CT image overlay 1100, 1150. In the present embodiment, users may rotate the scene to certain angles and draw a line by click two points on the screen. A 3D planar resection surface 1102, 1104 is automatically generated. This provides a means to initialize the resection surface simulation in a combined 2D and 3D manner to accommodate users who would prefer one over another.

In the present embodiment, 3D information may be provided to assist users to make decisions. For example, the left and right lobes' volume may be dynamically updated as the planar resection surface is updated. The liver volume and the relative volume are very important for both living donor liver transplantation and liver-tumor resection. Usually, the remaining lobe for the donor should keep at least ½ volume of the original liver. In living donor liver transplantation, ⅓~½ of the liver volume from the donor should be harvested for the recipient. In the present embodiment, the volume for each lobe and its ratio to the whole liver will be provided. Additionally, the blood-free volume may be provided. In the present embodiment, the blood-free volume may be obtained from the vessel models of the hepatic vein and the portal vein. If the remaining volume is not enough, the simulation will suggest not performing the surgery.

For cases such as removing small tumors locating at the boundary of the liver, planar resection is enough. To preserve more liver volume, resection using swept surfaces may be a better choice. However, planar resection and swept resection may fail, especially when the tumor is too close to certain critical vascular structures such as the MHV or when the tumor is huge. In such cases, freeform resection should be adopted.

Figure 12:
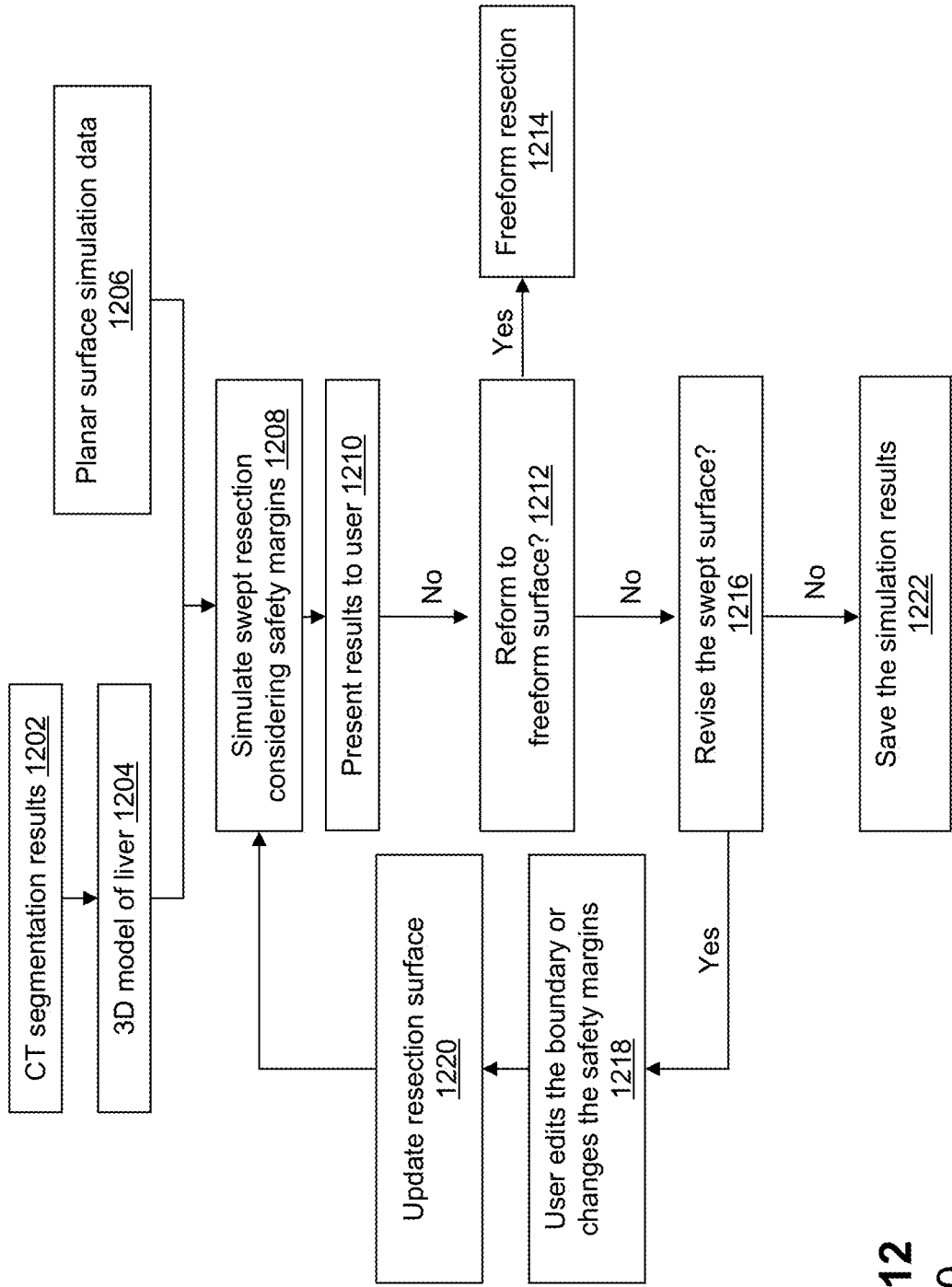
FIG. 12 depicts a flowchart embodying interactive surgery planning using a swept resection surface in accordance with the present embodiment.
Figure 13C:
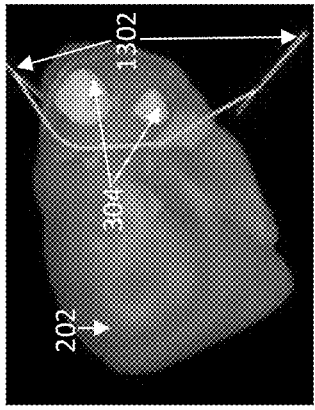
Figure 13F:
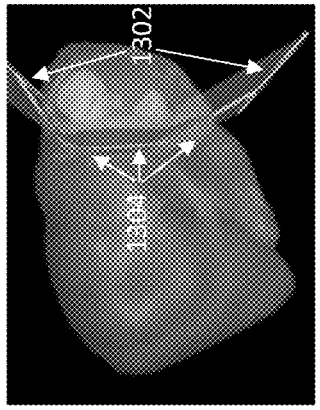
Figure 13I:
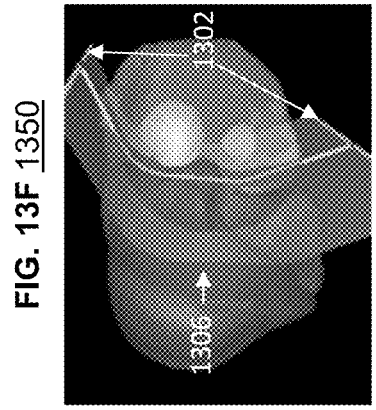
Figure 13B:
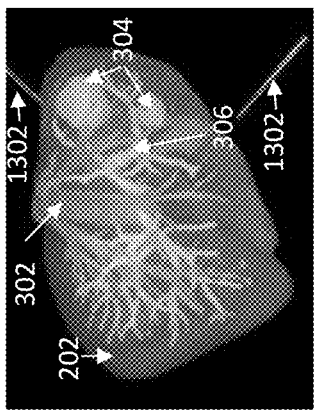
Figure 13E:
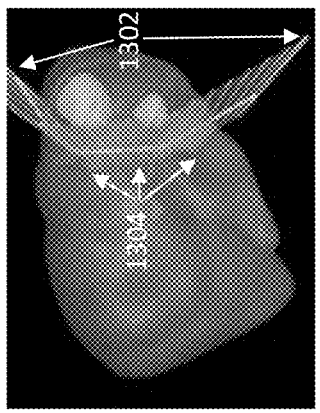
Figure 13H:
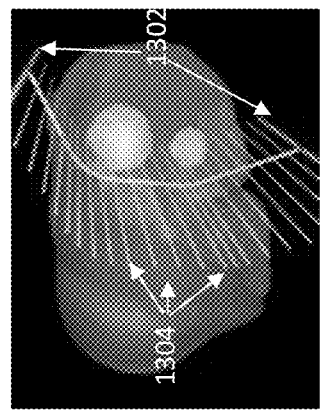
Figure 13A:
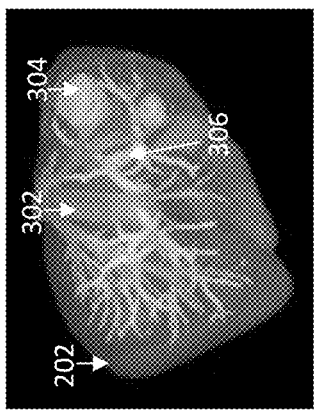
Figure 13D:
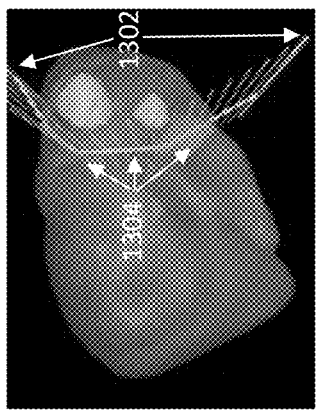
Figure 13G:
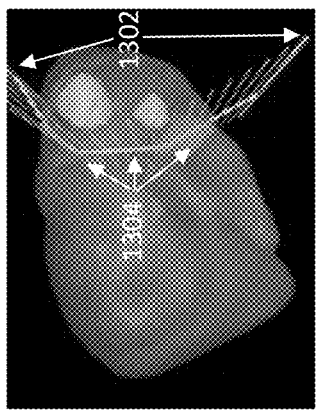
Figure 14A:
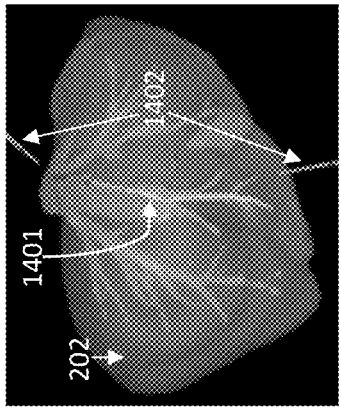
Figure 14B:
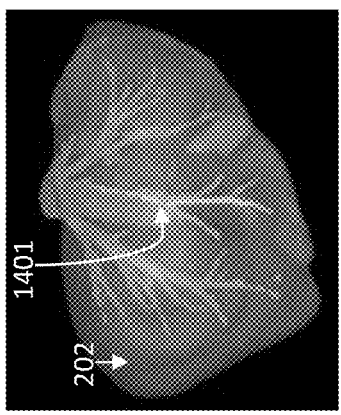
Figure 14C:
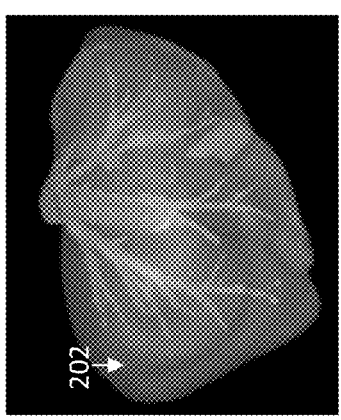
Figure 14D:
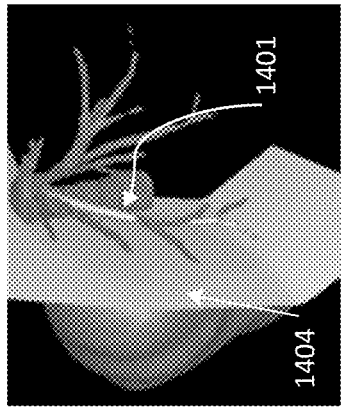
Figure 14E:
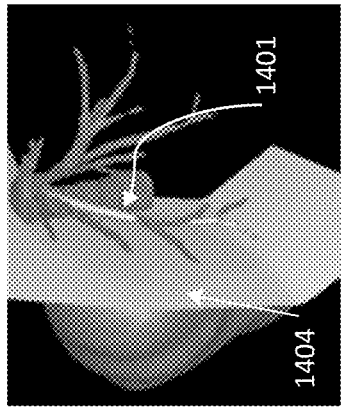
Figure 14F:
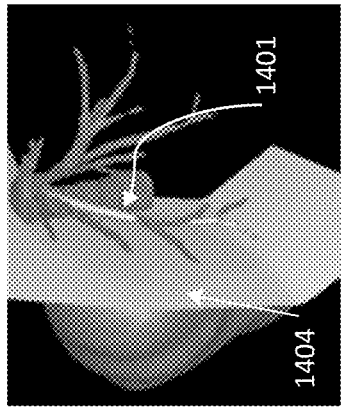

FIG. 12 depicts a flowchart embodying interactive surgery planning using a swept resection surface in accordance with the present embodiment. CT segmentation results 1202 may be used to derive a 3D model of the liver 1204. To initialize the swept resection simulation, simulation may use the position of the tumor, or modify the planar resection surface generated from a previous simulation 1206. The simulation defines two parallel lines in the coordinate space of the 3D model. These two parallel lines serve as the initial conditions for the simulation to simulate the swept resection. The simulation may consider safety margins around important features within the liver 1208, or other conditions that the user has indicated. After the simulation is complete, the swept resection simulation is presented to the user 1210. The user may decide if the swept resection surface needs to be reformed into a freeform surface 1212. The simulation will perform the freeform resection simulation 1214 based on the simulated swept resection surface 1208, that has been simulated. Alternatively, changes may be made to revise the swept surface 1216. The user may edit the boundary of the simulated swept resection surface, or change the safety margins around the important features 1218. The simulation will subsequently update the resection surface 1220 and simulate the swept resection 1208 considering the new boundary conditions and safety margins that the user has provided 1218. If the user is satisfied with the updated simulation 1212, the simulation results are saved for future reference 1222.

FIG. 13, comprising FIG. 13A to FIG. 13I, illustrates interactive surgery planning using a swept resection surface, in accordance with the present embodiment, wherein FIG. 13A to FIG. 13I illustrates a 3D visualization of a sequence of steps 1300, 1310, 1320, 1330, 1340, 1350, 1360, 1370, 1380 performed during interactive surgery planning using a swept resection surface 1306. Two parallel lines 1302 are first automatically generated according to the tumors' positions 304. The user may modify the position of the lines 1302. Subsequently a sweeping path 1304 is automatically generated connecting the two lines 1302. The swept path 1304 is generated such that the swept resection surface 1304, 1306 may keep safety margins to features 302, 304, 306 within the liver 202, in this case, the safety margins to all the tumors 304 are considered.

FIG. 14, comprising FIG. 14A to FIG. 14F, illustrates interactive surgery planning using a swept resection surface for hemihepatectomy, in accordance with the present embodiment, wherein FIG. 14A to FIG. 14F illustrate several 3D visualization views of the swept resection surface 1406. In FIG. 14A to FIG. 14F, the simulation automatically generates two parallel lines 1402 and the sweeping path 1404. In this case, the safety margin to the MHV 1401 is considered in the simulation.

In the present embodiment, the swept resection simulation provides a fully automatically generated surface 1306, 1406, which guarantees the safety margin to a feature within the liver 202. In the various embodiments, a safety margin to a tumor 304 and/or a safety margin to a feature 302, 304, 306 in the liver 306 may be considered. To modify a swept resection surface 1306, 1406, users only need to adjust the position of the two lines 1302, 1402. The simulation will automatically generate the sweeping path 1304, 1404 to generate a swept resection surface 1306, 1406. In addition, the construction of the swept resection surface 1306, 1406 is fast. Users may test different resection surfaces 1306, 1406 before making a final decision. As before, the 3D information including the resection lobe shape and the volume information of the resection may be dynamically updated. For example, in hemihepatectomy simulation, users may try both MHV-harvested solution and MHV-preserved solution before deciding which option is more feasible.

Figure 15:
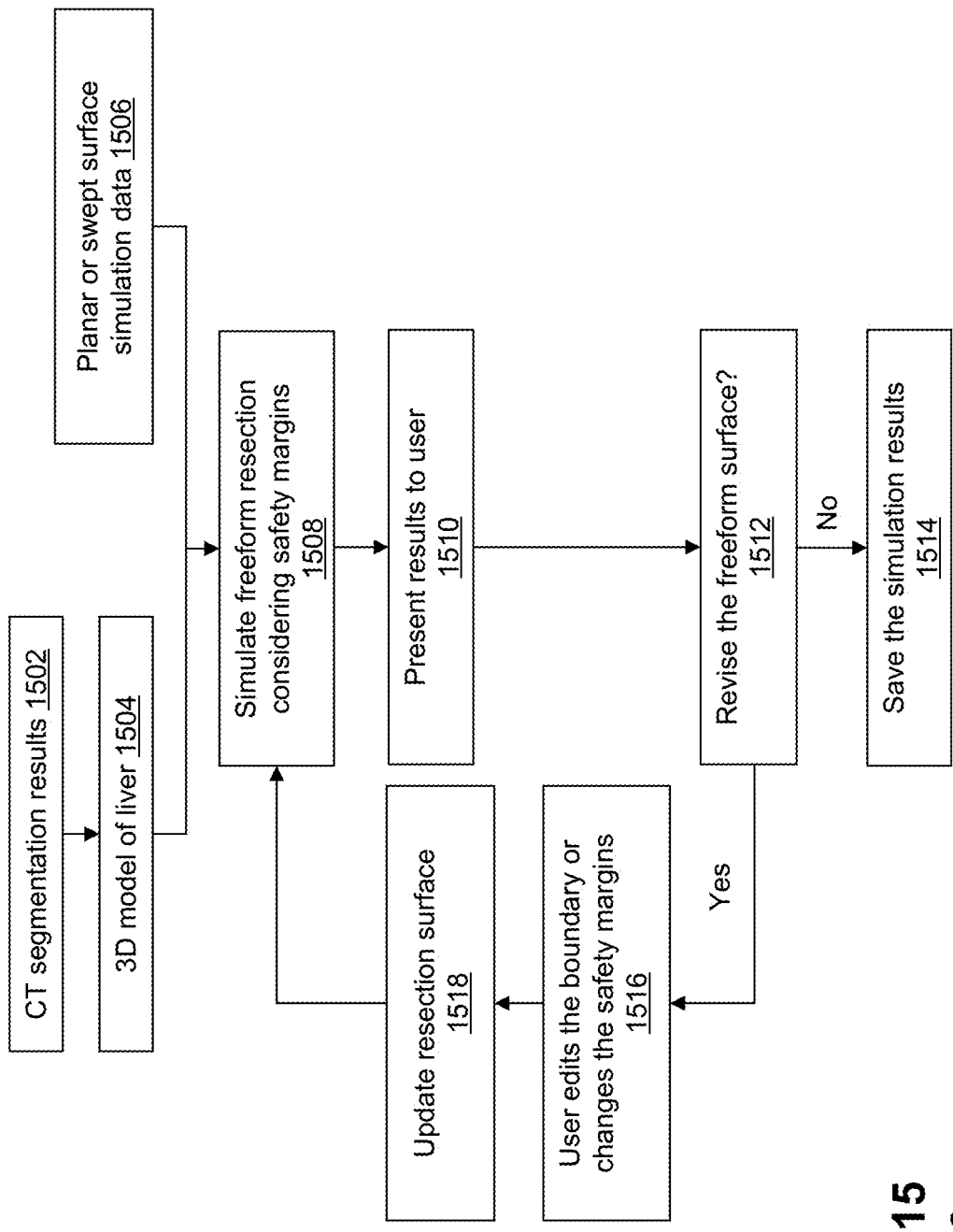
FIG. 15 depicts a flowchart embodying interactive surgery planning using a freeform resection surface in accordance with the present embodiment.

FIG. 15 depicts a flowchart embodying interactive surgery planning using a freeform resection surface in accordance with the present embodiment. CT segmentation results 1502 may be used to derive a 3D model of the liver 1504. To initialize the freeform resection simulation, the user may modify the planar or swept resection surface generated from a previous simulation 1206 by adjusting several control points on the boundary of the resection surface. The simulation may consider safety margins around important features within the liver 1508, or other conditions that the user has indicated. After the simulation is complete, the freeform resection simulation is presented to the user 1510. Changes may be made to revise the freeform surface 1512. The user may edit the boundary of the simulated freeform resection surface, or change the safety margins around the important features 1218. The simulation will subsequently update the resection surface 1518 and simulate the freeform resection 1508 considering the new boundary conditions and safety margins that the user has provided 1516. If the user is satisfied with the updated simulation 1512, the simulation results are saved for future reference 1514.

Figure 16:
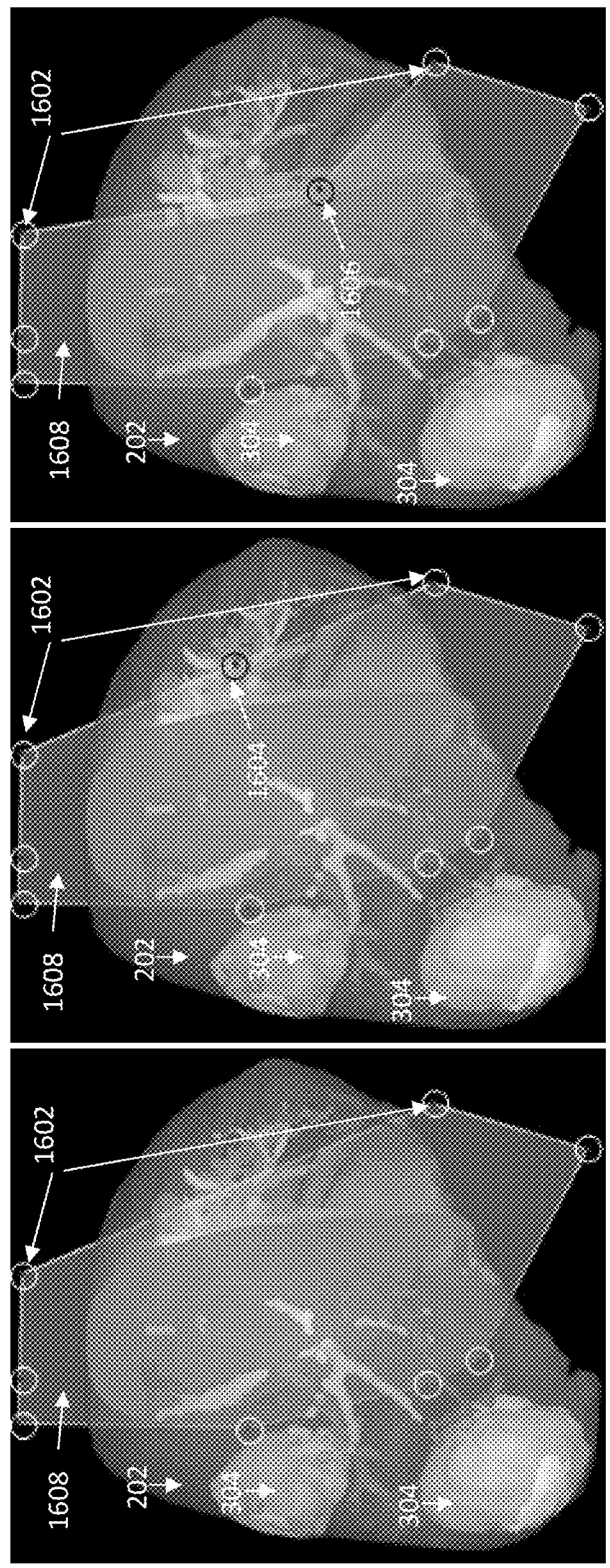
FIG. 16, comprising

FIG. 16, comprising FIG. 16A to FIG. 16C, illustrates interactive surgery planning using a freeform resection surface, in accordance with the present embodiment, wherein FIG. 16A to FIG. 16C illustrate a 3D visualization of a sequence of steps 1600, 1620, 1640 performed during interactive surgery planning using a freeform resection surface 1608. The user is able to adjust various control points 1602 along the boundary of the freeform resection surface 1608. In order to modify the freeform resection surface 1608, the user may select a point on the boundary of the freeform resection surface 1604 and move it to another position on the boundary 1606. This provides an intuitive and easy means of editing the freeform resection surface. As with previous resection simulations, the resection surface 1608 will be updated and considering the new boundary conditions 1602, 1606, and safety margins of the tumor 304 that the user has provided. 3D information of the liver 202 and volumetric information of the resection lobes may be provided to the user.

Figure 17:
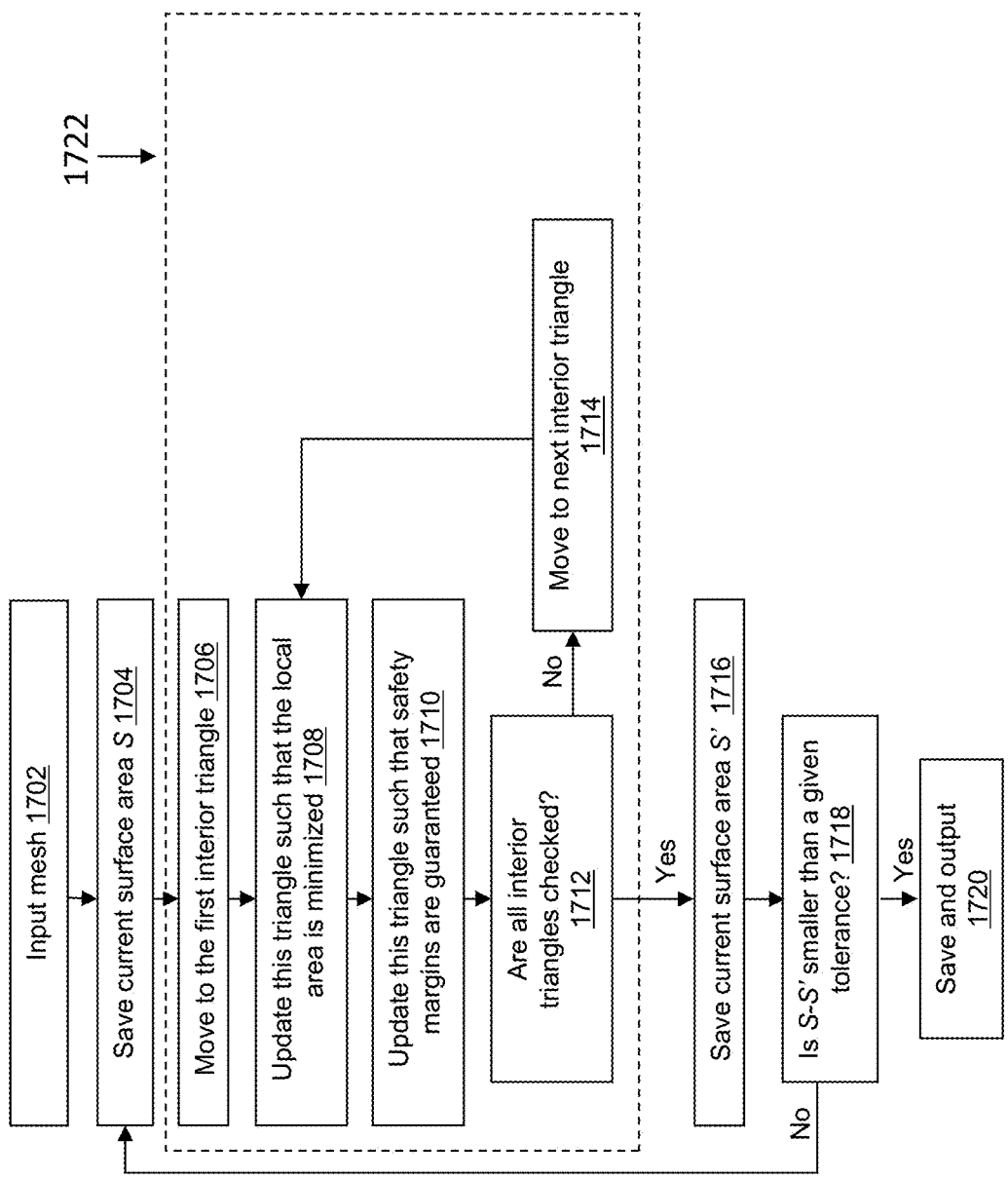
FIG. 17 depicts a method embodying optimizing a local area and a position of a resection surface based on a triangle-based algorithm in accordance with the present embodiment.

The method of local area optimization is to construct the surface from the boundary guaranteeing the safety margins as well as minimizing the surface area. FIG. 17 depicts a method embodying optimizing a local area and a position of a resection surface based on a triangle-based algorithm in accordance with the present embodiment. At step 1702, an input mesh is provided to the algorithm. The input mesh may comprise a previously simulated resection surface including planar or swept resection surfaces. At step 1704, the current surface area of the input mesh is saved as S. At step 1706, a first interior triangle on the resection surface is selected. At step 1708, the dimension of the triangle is updated such that the local area around the triangle is minimized. At step 1710, the position of the triangle is updated such that the safety margins are guaranteed, i.e., the triangle and the local area around the triangle are positioned outside of the safety margin around a predetermined feature of the liver. The steps of 1706 and 1712 are repeated for all interior triangles on the resection surface. The steps in dashed box 1722 represent one iteration. Before and after each iteration, the surface area changes from S to S' 1716. The algorithm will stop at step 1720 if and only if the change in area is smaller than a tolerance, S–S'<ε at step 1718. Since each time the area is reduced with a small amount, the algorithm may always stop in finite iterations. During an iteration cycle, all interior triangles are updated to minimize the local area and guarantee the safety margins.

Figure 18:
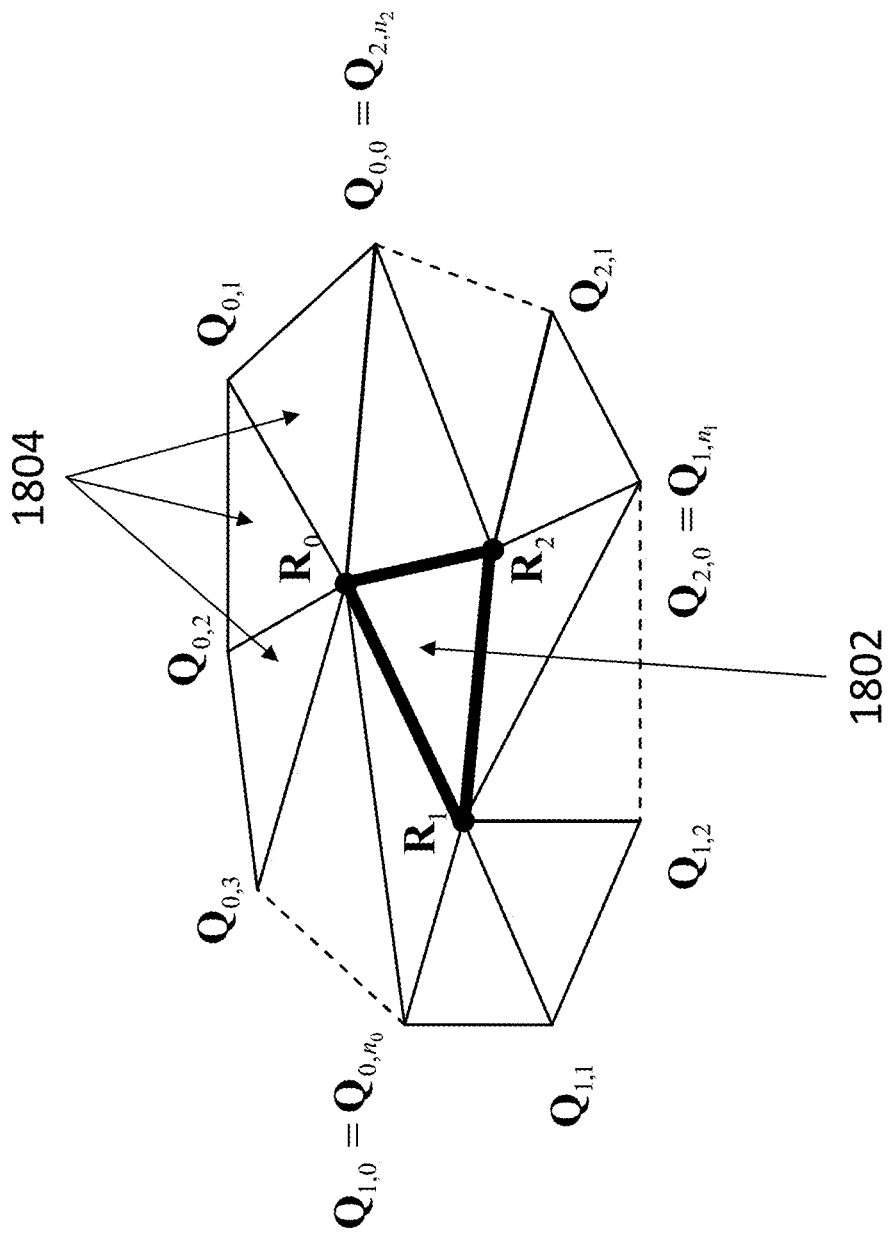
FIG. 18 illustrates the selection of a triangle on a resection surface for optimizing local area and position of the resection surface based on a triangle-based algorithm in accordance with the present embodiment.

FIG. 18 illustrates the selection of a triangle on a resection surface for optimizing local area and position of the resection surface based on a triangle-based algorithm in accordance with the present embodiment. For a triangle T 1802 with vertices $R_0$, $R_1$, $R_2$, its 1-ring neighboring region $\Phi_T$ contains all the triangles that use $R_i$ as one of its vertices 1804. $\Phi_T$ is bounded by the polygon defined by vertices $Q_{i,j}$, which are the neighboring vertices of $R_i$ for i=0, 1, 2. We perform the optimization in each local region $\Phi_T$ in two steps: minimizing the local area and adjusting the position of the vertices to guarantee the safety margin.

Figure 19A:
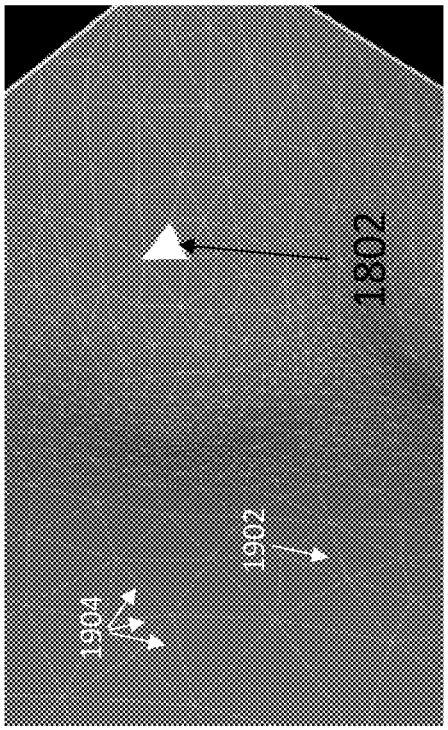
Figure 19B:
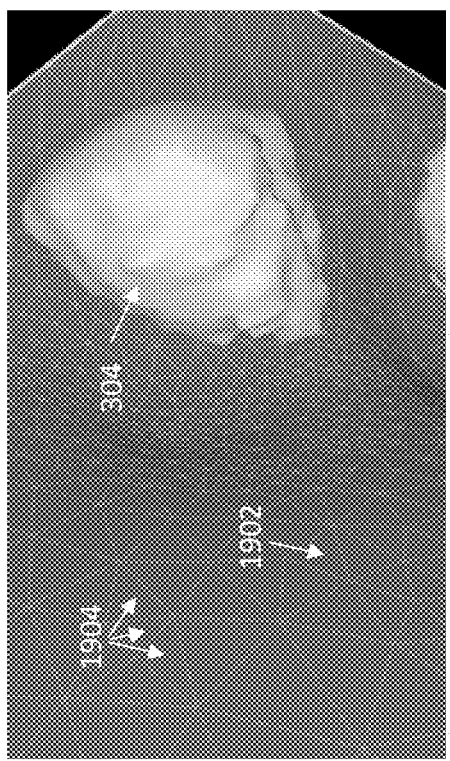
Figure 19C:
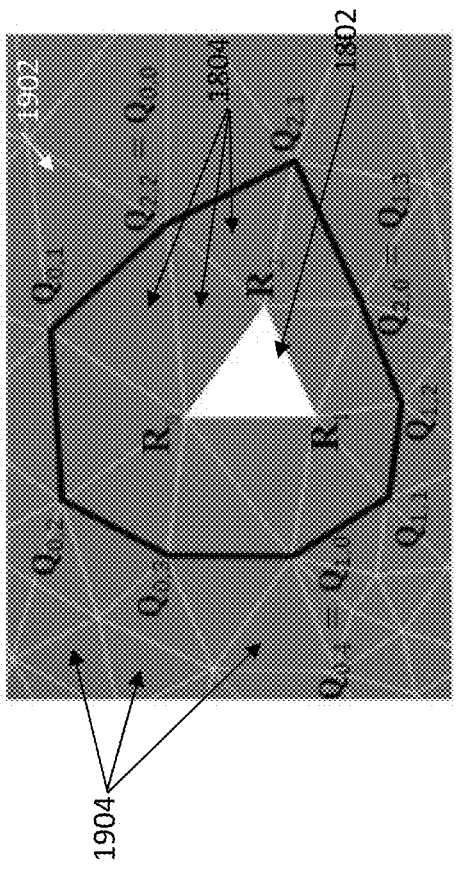

FIG. 19, comprising FIG. 19A to FIG. 19C, illustrates modelling a resection surface 1902 as a plurality of triangles 1904, in accordance with the present embodiment, wherein FIG. 19A illustrates the resection surface 1902 with the tumor 304, FIG. 19B illustrates the resection surface 1902 without the tumor 304, and FIG. 19C illustrates a close up of the selected triangle 1802.

The objective of the triangle based algorithm is to edit physical dimensions of the triangle T 1802, such that the area of $\Phi_T$ is minimized. The problem may be formulated as $$\min \ S(R_0, R_1, R_2) = \frac{1}{2}\sum_{t=0}^{2}\sum_{s=0}^{n_t-1}\sqrt{(R_t Q_{t,s} \otimes Q_{t,s}Q_{t,s+1})^2} + \qquad (1)$$

$$\frac{1}{2}\sum_{t=0}^{2}\sqrt{(R_t R_{t+1} \otimes R_{t+1}Q_{t+1,0})^2} + \frac{1}{2}\sqrt{(R_0 R_1 \otimes R_0 R_2)^2}.$$

Suppose, $$\frac{\partial F}{\partial R_k} = \left(\frac{\partial F}{\partial (R_k)_x}, \frac{\partial F}{\partial (R_k)_y}, \frac{\partial F}{\partial (R_k)_z}\right)^T \qquad (2)$$

The partial differential of the target function gives $$\frac{\partial S}{\partial R_k} = \frac{1}{4}\sum_{s=0}^{n_k-1}\frac{\frac{\partial}{\partial R_k}(R_k Q_{k,s} \otimes Q_{k,s}Q_{k,s+1})^2}{\sqrt{(R_k Q_{k,s} \otimes Q_{k,s}Q_{k,s+1})^2}} \qquad (3)$$

$$+\frac{1}{4}\frac{\frac{\partial}{\partial R_k}(R_k R_{k+1} \otimes R_{k+1}R_{k+2})^2}{\sqrt{(R_k R_{k+1} \otimes R_{k+1}R_{k+2})^2}} +$$

$$\frac{1}{4}\frac{\frac{\partial}{\partial R_k}(R_k R_{k+1} \otimes R_{k+1}Q_{k+1,0})^2}{\sqrt{(R_k R_{k+1} \otimes R_{k+1}Q_{k+1,0})^2}} + \frac{1}{4}\frac{\frac{\partial}{\partial R_k}(R_k R_{k-1} \otimes R_{k-1}Q_{k,0})^2}{\sqrt{(R_k R_{k-1} \otimes R_{k-1}Q_{k,0})^2}}$$

$$= \frac{1}{2}(D_k^1 + E_k^1 + F_k^1)R_k - \frac{1}{2}E_k^1 R_{k+1} - \frac{1}{2}F_k^1 R_{k-1} - \frac{1}{2}\left(\sum_{s=0}^{m_j-1}D_{k,s}^1 Q_{k,s}\right)$$

where $D_{k,s}^1$, $D_k^1$, $E_k^1$, $F_k^1$ are four 3×3 matrices as $$D_{k,s}^1 = \frac{|Q_{k,s}Q_{k,s+1}|^2 \begin{pmatrix} 1 & 0 & 0 \\ 0 & 1 & 0 \\ 0 & 0 & 1 \end{pmatrix} - (Q_{k,s}Q_{k,s+1})(Q_{k,s}Q_{k,s+1})^T}{\sqrt{(R_k Q_{k,s} \otimes Q_{k,s}Q_{k,s+1})^2}}, \qquad (4)$$

$$D_k^1 = \sum_{s=0}^{n_k-1} D_{k,s}^1, \qquad (5)$$

$$E_k^1 = \frac{|R_{k+1}R_{k+2}|^2 \begin{pmatrix} 1 & 0 & 0 \\ 0 & 1 & 0 \\ 0 & 0 & 1 \end{pmatrix} - (R_{k+1}R_{k+2})(R_{k+1}R_{k+2})^T}{\sqrt{(R_k R_{k+1} \otimes R_{k+1}R_{k+2})^2}} + \qquad (6)$$

$$\frac{|R_{k+1}Q_{k+1,0}|^2 \begin{pmatrix} 1 & 0 & 0 \\ 0 & 1 & 0 \\ 0 & 0 & 1 \end{pmatrix} - (R_{k+1}Q_{k+1,0})(R_{k+1}Q_{k+1,0})^T}{\sqrt{(R_k R_{k+1} \otimes R_{k+1}Q_{k+1,0})^2}},$$

$$F_k^1 = \frac{|R_{k-1}Q_{k,0}|^2 \begin{pmatrix} 1 & 0 & 0 \\ 0 & 1 & 0 \\ 0 & 0 & 1 \end{pmatrix} - (R_{k-1}Q_{k,0})(R_{k-1}Q_{k,0})^T}{\sqrt{(R_{k-1}R_k \otimes R_{k-1}Q_{k,0})^2}}. \qquad (7)$$

Setting the derivative to zero leads to a solution to the minimization problem. However, it is non-linear and thus is difficult to solve. We propose to use a local mechanism for iteratively approximating the solution. Suppose $$R = \begin{pmatrix} R_0 \\ R_1 \\ R_2 \end{pmatrix}, \quad (8)$$

$$A_1 = \begin{pmatrix} A_0^1 \\ A_1^1 \\ A_2^1 \end{pmatrix} = \begin{pmatrix} D_0^1 + E_0^1 + F_0^1 & -E_0^1 & -F_0^1 \\ -F_1^1 & D_1^1 + E_1^1 + F_1^1 & -E_1^1 \\ -E_2^1 & -F_2^1 & D_2^1 + E_2^1 + F_2^1 \end{pmatrix}, \quad (9)$$

$$B_1 = (B_0^1, B_1^1, B_2^1) = \left( \sum_{s=0}^{m_0-1} D_{0,s}^1 Q_{0,s}, \sum_{s=0}^{m_1-1} D_{1,s}^1 Q_{1,s}, \sum_{s=0}^{m_2-1} D_{2,s}^1 Q_{2,s} \right)^T. \quad (10)$$

Then we may reform the solution to $$\frac{\partial S}{\partial R} = \frac{1}{2} \begin{pmatrix} A_0^1 R - B_0^1 \\ A_1^1 R - B_1^1 \\ A_2^1 R - B_2^1 \end{pmatrix} = \frac{1}{2}(A_1 R - B_1) = 0 \Rightarrow R = (A_1)^{-1} B_1. \quad (11)$$

Since the right hand side of the equation also contains $R_i$, the above equation may not be considered to be an explicit solution for $R_i$. However, it gives us a way to update vertex $R_i$ iteratively. That is, we may update $R_i$ by $$\overline{R} = (A_1)^{-1} B_1. \quad (12)$$

The above equation provides a solution to the optimization problem. Such solution is highly depending on an initial value. Applying Laplacian operator and edge swapping before applying the area minimizing may help to provide a solution with a good surface quality.

After area minimizing, the total area for $\Phi_T$ is minimized. The next step is to update the triangle T 1802 until $\Phi_T$ may keep the safety margins to different tumors. This may be achieved in two steps:

Step 1: Move the triangle 1802 along its normal direction until the safety margins to tumors for this triangle 1802 are guaranteed.

Step 2: Move each vertex $R_i$ on the surface along its normal direction until the safety margins for triangles $\Delta R_i Q_{i,j} Q_{i,j+1}$ are guaranteed.

There are two key components in this operation for guaranteeing the safety margins. The first is that, we construct a minimal area mesh from the closed boundary using a triangle-based algorithm other than a vertex/edge-based algorithm. A vertex/edge-based algorithm minimizes the total area of the surface by minimizing the area around each vertex/edge. It may not guarantee the safety margin for each triangle on the surface, thus neither the safety margin for the whole resection surface. Therefore, the vertex/edge-based algorithm is not suitable for our application.

Step 2 is another crucial component to guarantee that $\Phi_T$ may keep the safety margins. Suppose X and Y are two neighboring triangles and the algorithm is adopted without Step 2. In each iteration, X is checked and the safety margins are guaranteed. But, in Y's turn, when guaranteeing the safety margin for Y, X is affected and the safety margins for X may not be satisfied. Thus, Step 2 is necessary.

Figure 20A:
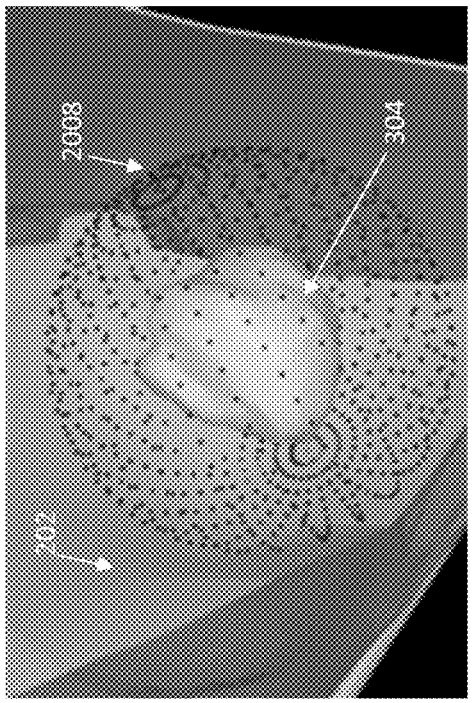
Figure 20C:
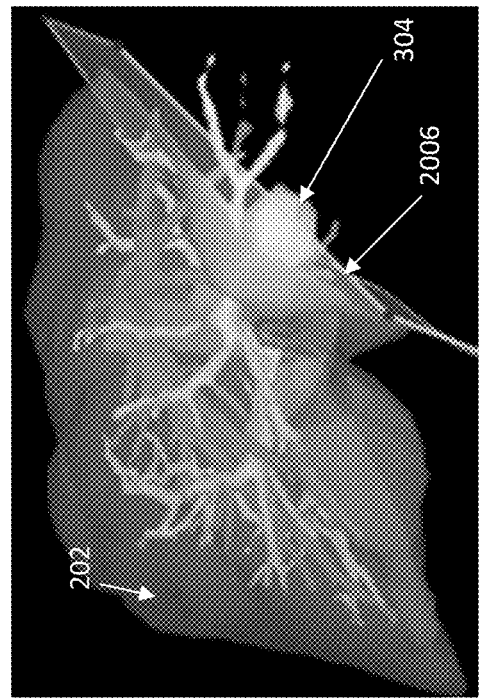
Figure 20B:
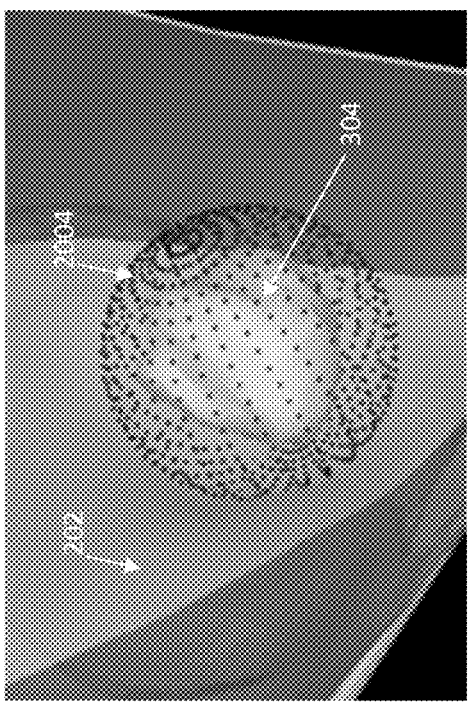
Figure 20D:
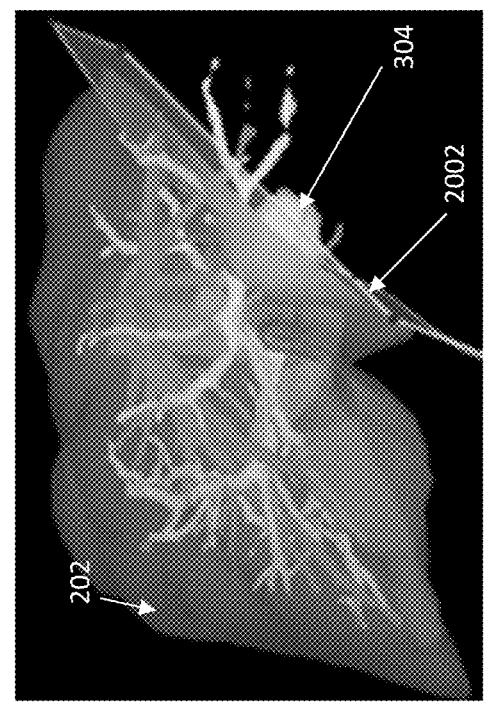

FIG. 20, comprising FIG. 20A to FIG. 20D, illustrates a 3D visualization 2000, 2020 of the safety margin 2004, 2008 around a tumor 304, in accordance with the present embodiment, wherein FIG. 20A and FIG. 20B illustrate an increase in the safety margin 2004, 2008 around a tumor 304 from 5 millimeters (mm) to 10 mm, respectively, and FIG. 20C and FIG. 20D illustrate a corresponding position of a resection surface 2002, 2006 with 5 mm and 10 mm safety margin around the tumor 304, respectively. The triangle based algorithm produces an area minimized resection surface 2002 that guarantees the safety margin 2004. When the safety margin is increased from 5 mm to 10 mm, the triangle based algorithm updates the previous resection surface 2002 to comply with the new safety margin 2008 while minimizing local area on the resection surface 2006.

Figure 21A:
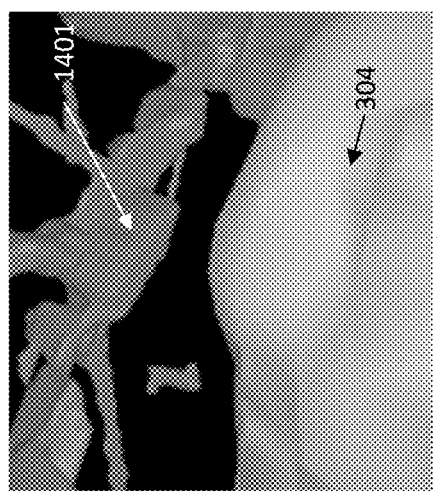
Figure 21B:
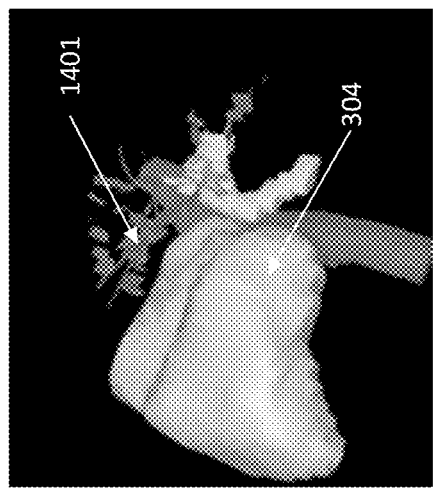
Figure 21C:
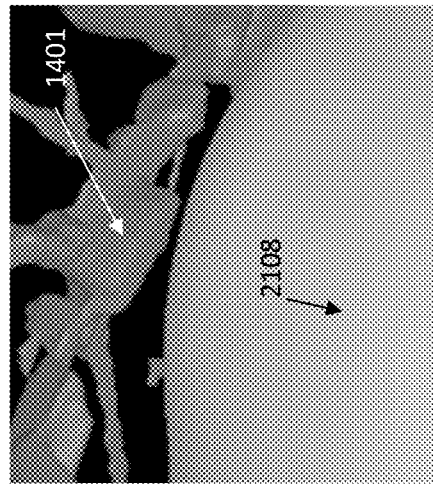
Figure 21D:
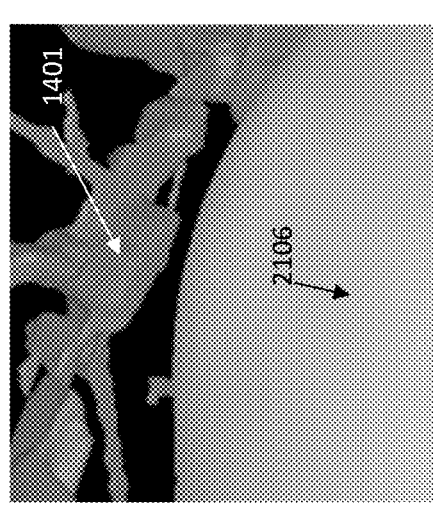
Figure 21E:
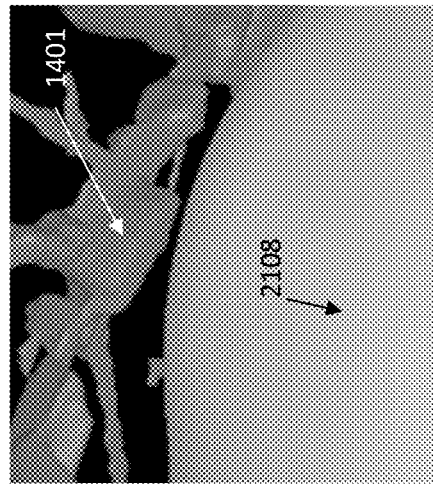

FIG. 21, comprising FIG. 21A to FIG. 21E, illustrates another 3D visualization of the safety margin around a tumor 304, in accordance with the present embodiment, wherein FIG. 21A and FIG. 21B illustrate the distance between the tumor 304 and the hepatic vein 302, and FIG. 21C to FIG. 21E illustrate a corresponding position of a resection surface 2004, 2006, 2008 when the safety margin around the tumor 304 is increased from 1 mm to 1.5 mm, and to 2 mm, respectively. In this embodiment, the tumor 304 is huge and is very close to the MHV 1401. Removing the MHV 1401 fails to provide enough remnant liver volume for the patient to survive. The idea of the precise surgery planning is to preserve as much volume as possible. Thus, surgeon needs to plan a resection surface 2104, 2106, 2108 separating the tumor 304 and MHV 1401. In FIG. 21A and FIG. 21B, there is only a small gap between the tumor 304 and MHV 1401. Using a planar resection surface or a swept resection surface as a starting point for the triangle based algorithm may not provide a solution. For complex cases such as this, a freeform resection surface may be chosen as the initial parameter for the triangle based algorithm to execute. In this case, 50% of the liver volume and the MHV 1401 may be preserved using the freeform resection. FIG. 21C to FIG. 21E shows how the resection surface changes after the user changes the safety margin. Similar to previous embodiments, when the safety margin is increased, the triangle based algorithm updates the previous resection surface 2104 to comply with the new safety margin 2106, 2108 while minimizing local area on the resection surface 2106, 2108.

Thus, in accordance with the present embodiment, a novel, advantageous and efficient method for surgical resection planning of a mass has been presented, which overcomes the drawback of prior art.

Some portions of the description are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "modelling", "storing", "determining", "optimizing", "updating", "repeating", "minimizing", or the like, refer to the action and processes of a computer system, or similar electronic device, that manipulates and transforms data represented as physical quantities within the computer system into other data similarly represented as physical quantities within the computer system or other information storage, transmission or display devices.

In addition, the present specification also implicitly discloses a computer program, in that it would be apparent to the person skilled in the art that the individual steps of the method described above may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a general purpose computer. The computer program when loaded and executed on such a computer effectively results in an apparatus that implements the steps of the preferred method.

While exemplary embodiments have been presented in the foregoing detailed description of the invention, it should be appreciated that a vast number of variations exist. For example, those skilled in the art will realize from the teachings herein that the present technology may also be applied to any part in the gastrointestinal tract or any part the skeletomuscular system.

It should further be appreciated that the exemplary embodiments are only examples, and are not intended to limit the scope, applicability, operation, or configuration of the invention in any way. Rather, the foregoing detailed description will provide those skilled in the art with a convenient road map for implementing an exemplary embodiment of the invention, it being understood that various changes may be made in the function and arrangement of elements and method of operation described in an exemplary embodiment without departing from the scope of the invention as set forth in the appended claims.

The invention claimed is:

1. A method executed by a computer for generating and displaying an improved surgical resection pre-operative planning of a mass, the mass comprising a plurality of features, the method comprising:
    modelling, by the computer, the mass including the plurality of features based on a plurality of physical dimensions, wherein the physical dimensions are determined based on image data of the mass received by the computer;
    determining, by the computer, a plurality of safety margins around the plurality of features within the mass;
    generating, by the computer, the improved surgical resection planning of the mass by:
    simulating, by the computer, a resection surface on the mass comprising a plurality of triangles, the simulated resection surface satisfying a selected one of the safety margins;
    optimizing, by the computer, local area and position of a first of the plurality of triangles on the resection surface based on a triangle-based algorithm by:
        minimizing the local area around the first of the plurality of triangles; and
        configuring a distance between the first of the plurality of triangles and a first of the plurality of features to be greater than a safety margin around the first of the plurality of features;
    updating, by the computer, dimensions of the plurality of triangles in order to update the simulation of the resection surface;
    repeating, by the computer, the steps of optimizing and updating for each of the plurality of triangles on the resection surface to generate the improved resection planning of the mass; and
    displaying, by the computer, the improved resection planning of the mass that includes the resection surface on the mass.

2. The method in accordance with claim 1, wherein the step of minimizing comprises:
    modelling the minimization of the local area around the first of the plurality of triangles as a mathematical function;
    applying a mathematical operation to the mathematical function; and
    approximating the mathematical function using an approximation to obtain a solution whereby the local area is minimized.

3. The method in accordance with claim 2, wherein the mathematical function is a partial differential equation.

4. The method in accordance with claim 2, wherein the mathematical operation includes a Laplacian operator with edge swapping.

5. The method in accordance with claim 2, wherein the approximation includes iterative approximation.

6. The method in accordance with claim 1, wherein the step of configuring comprises:
    considering if the first of the plurality of triangles is within the safety margin around the first of the plurality of features; and
    when the first of the plurality of triangles is within the safety margin around the first of the plurality of features, moving the first of the plurality of triangles along a direction until the distance between the first of the plurality of triangles and the first of the plurality of features is greater than the safety margin around the first of the plurality of features.

7. The method in accordance with claim 6, wherein the step of configuring further comprises, after considering and/or moving, the steps of:
    considering if the local area of the first of the plurality of triangles is within the safety margin around the first of the plurality of features; and
    when the local area of the first of the plurality of triangles is within the safety margin around the first of the plurality of features, moving each vertex of the first of the plurality of triangles along a direction until the distance between the local area around the first of the plurality of triangles is greater than the safety margin around the first of the plurality of features.

8. The method in accordance with claim 6, wherein the direction is along a normal of the triangle.

9. The method in accordance with claim 1, wherein the resection surface is a first of a plurality of resection surfaces.

10. The method in accordance with claim 9, wherein the plurality of resection surfaces include planar resection surfaces, swept resection surfaces and freeform resection surfaces.

11. The method in accordance with claim 1, wherein the resection surface is a second of a plurality of resection surfaces, the second of the plurality of resection surfaces simulated based on a first of the plurality of resection surfaces.

12. The method in accordance with claim 1, wherein the resection surface is a second of a plurality of resection surfaces, the second of the plurality of resection surfaces simulated based on a first of the plurality of resection surfaces simulated based on user modifications to the first of the plurality of resection surfaces.

13. The method in accordance with claim 1 wherein the plurality of physical dimensions is obtained from radiographic imagining of the mass including two dimensional computed tomography images.

14. A non-transitory computer readable storage medium having a computer program recorded therein, the program being executable by a computer apparatus to make the computer perform the procedure of generating and displaying an improved surgical resection pre-operative planning of a mass, the mass comprising a plurality of features, the procedure comprising:

modelling, by the computer apparatus, the mass including the plurality of features based on a plurality of physical dimensions, wherein the physical dimensions are determined based on image data of the mass received by the computer apparatus;

determining, by the computer apparatus, a plurality of safety margins around the plurality of features within the mass;

generating, by the computer apparatus, the improved surgical resection planning of the mass by:

simulating, by the computer apparatus, a resection surface on the mass comprising a plurality of triangles, the simulated resection surface satisfying a selected one of the safety margins;

optimizing, by the computer apparatus, local area and position of a first of the plurality of triangles on the resection surface based on a triangle-based algorithm by:

minimizing the local area around the first of the plurality of triangles; and configuring a distance between the first of the plurality of triangles and a first of the plurality of features to be greater than a safety margin around the first of the plurality of features;

updating, by the computer apparatus, dimensions of the plurality of triangles in order to update the simulation of the resection surface;

repeating, by the computer apparatus, the steps of optimizing and updating for each of the plurality of triangles on the resection surface to generate the improved resection planning of the mass; and displaying, by the computer apparatus, the improved resection planning of the mass that includes the resection surface on the mass.

15. The computer readable storage medium in accordance with claim 14, wherein the step of minimizing comprises:

modelling the minimization of the local area around the first of the plurality of triangles as a mathematical function;

applying a mathematical operation to the mathematical function; and approximating the mathematical function using an approximation to obtain a solution whereby the local area is minimized.

16. The computer readable storage medium in accordance with claim 15, wherein the mathematical function is a partial differential equation:

wherein the mathematical operation includes a Laplacian operator with edge swapping; and wherein the approximation includes iterative approximation.

17. The computer readable storage medium in accordance with claim 14, wherein the step of configuring comprises:

considering if the first of the plurality of triangles is within the safety margin around the first of the plurality of features; and when the first of the plurality of triangles is within the safety margin around the first of the plurality of features, moving the first of the plurality of triangles along a direction until the distance between the first of the plurality of triangles and the first of the plurality of features is greater than the safety margin around the first of the plurality of features.

18. The computer readable storage medium in accordance with claim 14 wherein the step of configuring further comprises, after considering and/or moving, the steps of:

considering if the local area of the first of the plurality of triangles is within the safety margin around the first of the plurality of features;

when the local area of the first of the plurality of triangles is within the safety margin around the first of the plurality of features, moving each vertex of the first of the plurality of triangles along a direction until the distance between the local area around the first of the plurality of triangles is greater than the safety margin around the first of the plurality of features.

19. The computer readable storage medium in accordance with claim 14 wherein the resection surface is a second of a plurality of resection surfaces, the second of the plurality of resection surfaces simulated based on a first of the plurality of resection surfaces.

20. The computer readable storage medium in accordance with claim 14 wherein the resection surface is a second of a plurality of resection surfaces, the second of the plurality of resection surfaces simulated based on a first of the plurality of resection surfaces simulated based on user modifications to the first of the plurality of resection surfaces.

* * * * *